United States Patent
Kuhl et al.

(10) Patent No.: US 9,993,432 B2
(45) Date of Patent: Jun. 12, 2018

(54) PHARMACEUTICAL DOSAGE FORM COMPRISING NIFEDIPINE OR NISOLDIPINE AND AN ANGIOTENSIN II ANTAGONIST AND/OR A DIURETIC

(75) Inventors: Alexander Kuhl, Beijing (CN); Erich Brendel, Solingen (DE); Frank Bröcker, Gevelsberg (DE); Adrian Funke, Berlin (DE); Andreas Ohm, Neuss (DE); Dennis Kvesic, Edmonton (CA); Thomas Volkmer, Berlin (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days. days.

(21) Appl. No.: 13/130,294

(22) PCT Filed: Nov. 19, 2009

(86) PCT No.: PCT/EP2009/008232
§ 371 (c)(1),
(2), (4) Date: Sep. 16, 2011

(87) PCT Pub. No.: WO2010/060564
PCT Pub. Date: Jun. 3, 2010

(65) Prior Publication Data
US 2012/0034272 A1   Feb. 9, 2012

(30) Foreign Application Priority Data
Nov. 27, 2008  (DE) .................. 10 2008 059 206

(51) Int. Cl.
| | |
|---|---|
| *A61K 9/20* | (2006.01) |
| *A61K 9/48* | (2006.01) |
| *A61K 9/24* | (2006.01) |
| *A61K 31/4422* | (2006.01) |
| *A61K 9/00* | (2006.01) |
| *A61K 9/28* | (2006.01) |
| *A61K 31/4178* | (2006.01) |
| *A61K 31/4184* | (2006.01) |
| *A61K 45/06* | (2006.01) |

(52) U.S. Cl.
CPC .......... *A61K 9/2031* (2013.01); *A61K 9/0004* (2013.01); *A61K 9/209* (2013.01); *A61K 9/2072* (2013.01); *A61K 9/2086* (2013.01); *A61K 9/2853* (2013.01); *A61K 9/2866* (2013.01); *A61K 31/4178* (2013.01); *A61K 31/4184* (2013.01); *A61K 31/4422* (2013.01); *A61K 45/06* (2013.01)

(58) Field of Classification Search
CPC .............. A61K 2300/00; A61K 9/0004; A61K 31/4422
See application file for complete search history.

(56) References Cited

U.S. PATENT DOCUMENTS

| | | | |
|---|---|---|---|
| 3,644,627 A | 2/1972 | Bossert et al. | |
| 4,327,725 A | 5/1982 | Cortese et al. | |
| 4,576,604 A * | 3/1986 | Guittard et al. | ............... 424/473 |
| 4,612,008 A | 9/1986 | Wong et al. | |
| 4,673,405 A * | 6/1987 | Guittard et al. | ............... 424/473 |
| 4,765,989 A | 8/1988 | Wong et al. | |
| 4,783,337 A | 11/1988 | Wong et al. | |
| 4,842,867 A | 6/1989 | Ayer et al. | |
| 4,892,741 A | 1/1990 | Ohm et al. | |
| 4,948,592 A | 8/1990 | Ayer et al. | |
| 5,082,668 A | 1/1992 | Wong et al. | |
| 5,160,744 A | 11/1992 | Jao et al. | |
| 5,178,867 A | 1/1993 | Guittard et al. | |
| 5,204,121 A | 4/1993 | Bucheler et al. | |
| 5,543,154 A | 8/1996 | Rork et al. | |
| 6,004,582 A | 12/1999 | Faour et al. | |
| 6,086,919 A | 7/2000 | Bauer et al. | |
| 6,294,201 B1 | 9/2001 | Kettelhoit et al. | |
| 6,555,136 B2 | 4/2003 | Midha | |
| 6,919,373 B1 | 7/2005 | Lam et al. | |
| 7,022,344 B1 * | 4/2006 | Kothrade et al. | ............. 424/486 |
| 7,037,526 B1 * | 5/2006 | Krumme | ............... A61K 9/7007 |
| | | | 424/484 |
| 8,153,160 B2 | 4/2012 | Ohm et al. | |
| 2003/0044466 A1 * | 3/2003 | Markey et al. | ............... 424/469 |

(Continued)

FOREIGN PATENT DOCUMENTS

| | | |
|---|---|---|
| AU | 2003227472 A1 | 3/2003 |
| CA | 2352436 A1 | 7/2000 |

(Continued)

OTHER PUBLICATIONS

Hayashi et al., "Disparate Effects of Calcium Antagonists on Renal Microcirculation," Hypertens. Res., 1996, vol. 19, 31-36.
Jamerson et al., "Benazepril plus Amlodipine or Hydroxhlorothiazide for Hypertension in High-Risk Patients," N. Engl. J. Med. 2008, vol. 359, No. 23, 2417-2428.
Lippold, B.C., "Controlled Release Products: Approaches of Pharmaceutical Technology," Düsseldor, Wiss. Veri. Ges., 1989, 39-57.
Santus et al., "Osmotic Drug Delivery: A Review of the Patent Literature," Journal of Controlled Release, 1995, vol. 35, 1-21.
Verma et al., "Osmotically Controlled Oral Drug Delivery," Drug Development & Industrial Pharmacology 2000, vol. 26, No. 7, 695-708.

(Continued)

*Primary Examiner* — Robert T. Crow
*Assistant Examiner* — John P Nguyen
(74) *Attorney, Agent, or Firm* — Morrison & Foerster LLP

(57) ABSTRACT

The present invention relates to a pharmaceutical dosage form comprising an active ingredient combination of nifedipine or nisoldipine and at least one angiotensin II antagonist and/or at least one diuretic, characterized in that nifedipine or nisoldipine is released in the body in a controlled (modified) manner and the angiotensin II antagonist and/or the diuretic is released rapidly (immediate release (IR)), and also to processes for their preparation, to their use as medicaments and to their use for the prophylaxis, secondary prophylaxis or treatment of disorders.

26 Claims, No Drawings

(56) References Cited

U.S. PATENT DOCUMENTS

| | | |
|---|---|---|
| 2003/0161882 A1 | 8/2003 | Waterman |
| 2004/0115134 A1 | 6/2004 | Merisko-Liversidge |
| 2005/0008702 A1 | 1/2005 | Faour et al. |
| 2005/0226928 A1* | 10/2005 | Lodin et al. ............... 424/469 |
| 2005/0266080 A1 | 12/2005 | Desai et al. |
| 2007/0026065 A1* | 2/2007 | Benke et al. ................ 424/468 |
| 2007/0128281 A1* | 6/2007 | Patel .......................... 424/473 |
| 2009/0093542 A1* | 4/2009 | Cooper ....................... 514/551 |
| 2009/0214664 A1* | 8/2009 | Ohm et al. .................. 424/497 |
| 2010/0041644 A1 | 2/2010 | Sánchez et al. |
| 2010/0112052 A1* | 5/2010 | Chen ..................... A61K 9/209 424/468 |
| 2014/0010876 A1* | 1/2014 | Benke et al. ................ 424/472 |

FOREIGN PATENT DOCUMENTS

| | | |
|---|---|---|
| DE | 3417113 | 11/1984 |
| DE | 19747261 | 4/1999 |
| EP | 0299211 | 1/1989 |
| EP | 0339811 A2 | 4/1989 |
| EP | 0386440 | 9/1990 |
| EP | 0459136 A1 | 4/1991 |
| EP | 1306088 A1 | 6/1994 |
| EP | 0776660 A2 | 4/1997 |
| EP | 1024793 | 8/2000 |
| EP | 1336407 | 8/2003 |
| EP | 1413315 | 4/2004 |
| GB | 2140687 | 12/1984 |
| IE | 56515 A1 | 5/1983 |
| JP | S62-267221 | 11/1987 |
| JP | H09-504806 | 5/1997 |
| JP | 2000-516637 | 12/2000 |
| JP | 2001-520985 | 11/2001 |
| JP | 2004-002348 | 1/2004 |
| WO | 199210097 | 6/1992 |
| WO | WO 9210097 A1 * | 6/1992 |
| WO | 199300071 A1 | 1/1993 |
| WO | 199303711 A1 | 3/1993 |
| WO | 96/07400 | 3/1996 |
| WO | 98/53802 | 12/1998 |
| WO | 99/21536 | 5/1999 |
| WO | 00/43370 | 7/2000 |
| WO | 01/51037 | 7/2001 |
| WO | 2003035039 | 5/2003 |
| WO | 2003080057 | 10/2003 |
| WO | 03/097045 | 11/2003 |
| WO | 03/097067 | 11/2003 |
| WO | 2003097045 A1 | 11/2003 |
| WO | 2004/075892 | 9/2004 |
| WO | 2005009412 | 2/2005 |
| WO | 2005084648 A1 | 2/2005 |
| WO | 2005070398 A2 | 8/2005 |
| WO | 2005079751 A2 | 9/2005 |
| WO | 2006/086456 | 8/2006 |
| WO | 2007003330 A2 | 1/2007 |
| WO | 2008035360 A2 | 3/2008 |
| WO | 2008044862 A1 | 4/2008 |
| WO | 2008045006 A1 | 4/2008 |
| WO | WO 2008044862 A1 * | 4/2008 |
| WO | 2009054550 A1 | 4/2009 |

OTHER PUBLICATIONS

Verma et al., "Formulation Aspects in the Development of Osmotically Controlled Oral Drug Delivery Systems," Journal of Controlled Release 2002, vol. 79, 7-27.

Verma et al., "Osmotic Pumps in Drug Delivery," Crit. Rev. in Therapeutic Drug Carrier Syststems 2004, vol. 21, No. 6, 477-520.

Kubo et al., "Nonpeptide Angiotensin II Receptor Antagonists: Synthesis and Biological Activity of Potential Prodrugs of Benzimidazole-7-carboxylic Acids," Med. Chem. 1993 vol. 36, No. 16, 2343-2349.

Hasabe et al., "Controlled-release nifedipine and candesartan low-dose combination therapy in patients with essential hypertentions: the NICE combi (Nifedipine and Candesartan Combination) Study," J. of Hypertension, 2005, vol. 23, No. 2, pp. 445-453.

U.S. Appl. No. 11/922,745, filed Mar. 13, 2009.

Swanson et al. "Nifedipine Gastrointestinal Therapeutic System," Am J. Med, Dec. 21, 1987, 83(sup 6B):3-9.

* cited by examiner

PHARMACEUTICAL DOSAGE FORM COMPRISING NIFEDIPINE OR NISOLDIPINE AND AN ANGIOTENSIN II ANTAGONIST AND/OR A DIURETIC

This application is the National Stage of International Patent Application Number PCT/EP2009/008232, filed Nov. 19, 2009, which claims the benefit of priority of German Provisional Application Number DE 10 2008 059 206.4, filed Nov. 27, 2008.

The present invention relates to a pharmaceutical dosage form comprising an active ingredient combination of nifedipine or nisoldipine and at least one angiotensin II antagonist and/or at least one diuretic, characterized in that nifedipine or nisoldipine is released in the body in a controlled (modified) manner and the angiotensin II antagonist and/or the diuretic is released rapidly (immediate release (IR)), and also to processes for their preparation, to their use as medicaments and to their use for the prophylaxis, secondary prophylaxis or treatment of disorders.

The primary target of the pharmacological therapy of hypertension is to control the blood pressure in order to prevent sequelae such as cardiovascular disorders, cerebrovascular disorders and damage to end organs. The initial adjustment of patients suffering from hypertension is generally initiated with hypertension monotherapy (European Society of Hypertension Guidelines 2007, Joint National Committee VII (JNC VII) Guidelines, Japanese Society of Hypertension (JSH) Guidelines). It is to be expected that, when hypertension monotherapy is employed, a number of patients will not achieve the required target blood pressure, as described in the international guidelines. In the United States of America, about 33% of hypertension patients adjusted to monotherapy are readjusted to a second-line therapy within the first year.

Calcium antagonists such as, for example, nifedipine and nisoldipine are, as established active ingredients, successfully used in hypertension therapy. The examples shown are familiar to the person skilled in the art and are described in the relevant literature. Through their direct effect on the arterial blood vessels, they reduce the blood pressure reliably in a large proportion of patients. However, they bring about an increase in the filtration pressure in the kidney through preferential dilatation of the afferent arterioles. Where the kidney has previously been damaged, this may lead to an increased stress on the filtration apparatus and be manifested by proteinuria in patients. This effect can be prevented by addition of a therapeutically effective dose of an angiotensin II antagonist. Suitable angiotensin II antagonists are all known angiotensin II antagonists such as, for example, azilsartan, candesartan, embursartan, eprosartan, irbesartan, losartan, telmisartan, valsartan or olmesartan. The examples shown are familiar to the person skilled in the art and are described in the relevant literature. Since angiotensin II antagonists also have a dilating effect in the region of the efferent arteriole, additional administration of these substances can prevent the unwanted increase in the filtration pressure.

As disclosed in Hayashi K; Nagahama T, Oka K, Epstein M, Sarute T: Disparate effects of calcium antagonists on renal microcirculation. *Hypertens Res* 1996: 19: 31-36, combination of nifedipine and/or nisoldipine with an angiotensin II antagonist brings about a very good reduction in blood pressure together with lower stress on the kidney. This represents a considerable therapeutic advance. It is additionally possible by the combination also to reduce other side effects such as the peripheral oedemas which occur with calcium antagonists, and the stimulation, caused by reflex release of noradrenaline, of the sympathetic nervous system. Furthermore, recent study results (ACCOMPLISH; American Cardiolygy Congress Jamerson K A, et al. 31 Mar. 2008; Chicago, Ill.) show that fixed combinations are advantageous not only with respect to blood pressure control rates but, when a calcium antagonists is employed, also with respect to a reduction of cardiovascular morbidity and mortality.

In cases of diseases which require treatment over a lengthy period, or for the long-term prophylaxis of diseases, it is desirable to keep the frequency of intake of medicaments as low as possible. This is not only more convenient for the patient, it also increases the reliability of treatment by reducing the disadvantages of irregular intake. The desired reduction in the frequency of intake, for example from administration twice a day to once a day, can be achieved by prolonging the therapeutically effective plasma levels by modified release of active ingredients from the dosage forms.

After intake of dosage forms with modified active ingredient release it is additionally possible to reduce, by smoothing the course of the plasma levels (minimizing the so-called peak-trough ratio), i.e. by avoiding high plasma active ingredient concentrations which are to be observed frequently after administration of fast-release pharmaceutical forms, the occurrence of unwanted side effects which correlate with the concentration peaks.

It is advantageous especially for the long-term therapy or prophylaxis and secondary prophylaxis of cardiovascular disorders to have the active ingredients available in a form which, through a modified release of active ingredients, leads to a reduction in the peak-trough ratio and makes administration once a day possible.

In the development of formulations, account must also be taken of the physicochemical and biological properties of the active ingredients, for example the relatively low water solubility of nifedipine (approx. 9 mg/l) and the plasma half-life of about 2 hours. Accordingly, special pharmaceutical formulations with which nifedipine and/or nisoldipine undergoes a modified release, taking account of its physicochemical and biological properties, are necessary for the desired administration once a day.

The angiotensin II antagonists in the form of their commercial products are all marketed as fast-release (immediate-release (IR)) formulations because, despite their short dominant plasma half-life, their effect persists for more than 24 hours. It is thus desirable to provide a pharmaceutical dosage form comprising at least one angiotensin II antagonist and nifedipine or nisoldipine, where the angiotensin II antagonist is released rapidly and the nifedipine or nisoldipine is released in modified form.

In view of the biological properties of nifedipine and/or nisoldipine and the angiotensin II antagonists, it is crucial for both active ingredients to be absorbed from the low sections of the bowel without significant loss of bioavailability. This is the case with only about 30-50% of all active ingredients, and therefore appropriate selection of the combination active ingredients is crucially important for developing an IR/slow-release combination product.

Diuretics are medicaments used for eliminating water from the human or animal body. In some instances, elimination of salts, too, is increased. This results in a reduction of plasma volume and peripheral resistance. Diuretics are primarily employed for lowering blood pressure. There are various types of diuretics. Carboanhydrase inhibitors (acetazolamide): blockade of proton secretion and sodium bicarbonate re-absorption, mainly at the proximal tubulus. Nowadays use limited almost exclusively to ophthalmology for the treatment of glaucomas. Loop diuretics (furosemide, torasemide, bumetanide, etacrynic acid, piretanide): reversible inhibition of an Na/2Cl/K carrier system at the thick ascending limb of the loop of Henle. Potassium-sparing diuretics (amiloride, triamterene): blockade of the Na channels at the late distal tubulus and at the collecting tube, inhibition of Na re-absorption, as a consequence reduced K secretion. Aldosterone antagonists (spironolactone, potassium canreonate, eplerenone): competitive binding at the aldosterone receptor, as a consequence inhibition of Na re-absorption and K secretion, used for ascites associated with cirrhosis of the liver and as additional therapeutic for chronic heart failure. Thiazide diuretics and other sulphonamide diuretics (hydrochlorothiazide (=HCTZ), chlorothiazide, chlorthalidone, xipamide, indapamide, mefruside): reversible inhibition of the Na—Cl cotransport at the early distal tubulus (luminal), inhibition of carboanhydrase, reduction of GFR, hydrochlorothiazide frequently employed in combination with antihypertensive agents. The addition of a diuretic such as, for example, HCTZ in monotherapy enhances the hypotensive action of the combination.

Combinations of a diuretic and angiotensin II antagonists are known to the person skilled in the art, for example from EP 1 306 088 B (candesartan and furosemide), but also the following fixed-dose combinations for treating high blood pressure such as, for example, Hyzaar® (=losartan potassium plus HCTZ) from Merck, Co-Diovan® (=valsartan plus HCTZ) from Novartis or Boehringer's Micardis Plus® (=telmisartan plus HCTZ).

Combinations of an angiotensin II antagonist and, firstly, calcium channel blockers or, secondly, diuretics are known to the person skilled in the art, for example from WO 92/10097. Explicitly described are the combinations of eprosartan and nifedipine and eprosartan and hydrochlorothiazide. Specifically disclosed are fast-release hard gelatine capsules and tablets.

Dosage forms releasing the active compounds nifedipine or nisoldipine in combination with an angiotensin II antagonist in modified/delayed form and their preparation are described, for example, in WO 2007/003330. In these formulations, both nifedipine and the angiotensin II antagonist are released in delayed form.

The diuretics have plasma half-lives and activities of various durations; however, most are, as commercial products, marketed as immediate release (IR) formulations to be taken once every day. It is thus desirable to provide a pharmaceutical dosage form comprising at least one angiotensin II antagonist and/or a diuretic and nifedipine or nisoldipine, where the angiotensin II antagonist and/or the diuretic is released rapidly and the nifedipine or nisoldipine is released in modified form.

Various methods are known for producing pharmaceutical dosage forms with modified release; see, for example, B. Lippold in "Oral Controlled Release Products: Therapeutic and Biopharmaceutic Assessment" Editors U. Gundert-Remy and H. Möller, Stuttgart, Wiss. Verl.-Ges., 1989, 39-57.

Dosage forms releasing nifedipine or nisoldipine in modified/delayed form and their preparation are described, for example, in EP 0 299 211, EP 0 386 440, EP 0 776 660 and WO 2003/080057.

Particularly suitable dosage forms with modified/delayed release of the active ingredient nifedipine or nisoldipine are based on osmotic release systems. In these, cores, for example capsules or tablets, preferably tablets, are surrounded by a semipermeable membrane which has at least one orifice. The water-permeable membrane is impermeable for components of the core, but allows water to enter the system from outside by osmosis. The water which has penetrated in then releases, by the resulting osmotic pressure, the active ingredient in dissolved or suspended form from the orifice(s) in the membrane. The overall active ingredient release and the release rate can be controlled substantially via the thickness and porosity of the semipermeable membrane, the composition of the core and the number and size of the orifice(s). Advantages, formulation aspects, use forms and information on production processes are described inter alia in the following publications:

Santus, G., Baker, R. W., "Osmotic drug delivery: a review of the patent literature", Journal of Controlled Release 35 (1995), 1-21

Verma, R. K., Mishra, B., Garg, S., "Osmotically controlled oral drug delivery", Drug Development and Industrial Pharmacy 26 (7), 695-708 (2000)

Verma, R. K., Krishna, D. M., Garg, S., "Formulation aspects in the development of osmotically controlled oral drug delivery systems", Journal of Controlled Release 79 (2002), 7-27

Verma, R. K., Arora, S., Garg, S., "Osmotic pumps in drug delivery", Critical Reviews in Therapeutic Drug Carrier Systems 21 (6) (2004), 477-520

U.S. Pat. No. 4,327,725, U.S. Pat. No. 4,765,989, US 20030161882, EP 1 024 793.

Coated osmotic release systems are likewise known. Thus, EP 0 339 811 describes an osmotic release system consisting of a cellulose acetate coat which comprises nifedipine and swelling agent in the core and is surrounded by a mantle coating of HPMC (hydroxypropylmethylcellulose) having a layer thickness of 0.0025 cm. U.S. Pat. No. 4,948,592, WO 93/03711 and WO 93/00071 describe osmotic release systems comprising a proportion of active ingredient in the core with a delayed release profile and a proportion of the same active ingredient in the mantle coating which can be released directly. Here, the mantle coatings comprise in each case only a small part of the total amount of active ingredient required for pharmaceutical activity. Active ingredient combinations having various active ingredients or mantle coatings comprising angiotensin II antagonisten and/or a diuretic are not described.

It is an object of the present invention to provide a stable pharmaceutical formulation comprising nifedipine or nisoldipine and at least one angiotensin II antagonist and/or at least one diuretic, where the angiotensin II antagonist and/or the diuretic is released rapidly (IR) and nifedipine or nisoldipine is release in delayed form and which thus corresponds to the release behaviour of the known individual formulations.

Surprisingly, with the present invention it is possible to provide a stable pharmaceutical dosage form comprising an angiotensin II antagonist and/or a diuretic in an amount sufficient for its pharmaceutical action, where the angiotensin II antagonist and/or the diuretic is released rapidly, and comprising nifedipine or nisoldipine, where the nifedipine or nisoldipine can be released in a controlled (modified) manner. To ensure rapid release of the angiotensin II antagonist and/or the diuretic, it is necessary to incorporate it into the outer mantle layer of the dosage form. Owing to the amount of active ingredient required, this requires a much thicker mantle layer than the film layers known to date of osmotic release systems, which do not comprise any active ingredient. Thus, the behaviour of the outer mantle layer is influenced strongly by the properties of the active ingredient used. Especially in the case of cellulose acetate-based osmotic active ingredient release systems, the application of thick layers is critical owing to the smooth and hydrophobic surface. Also, the invention surprisingly overcomes the general problem of poor coherence of thick layers, and the mantle layer is not observed to flake off. The requirement to provide uniform dosage forms with respect to the amount of active ingredient in the mantle layer (content uniformity) is also met. This is the more difficult the thicker the mantle layer, since usually variations increase with increasing layer thickness. Furthermore, thick mantle layers require long process times under moist-warm conditions, which may accelerate chemical decomposition reactions of the active ingredient in the mantle layer. Surprisingly, the dosage form according to the invention achieves an active ingredient release behaviour which corresponds approximately to that of the known individual formulations, i.e. rapid release (IR) of the angiotensin II antagonists and/or diuretics and controlled (modified, delayed) release of nifedipine or nisoldipine. Accordingly, the dosage forms according to the invention can be considered to be biologically equivalent to known individual formulations of the same dose. Furthermore, the stability of the angiotensin II antagonist and/or diuretic during the spraying-on process according to the inventive preparation process is, surprisingly, ensured.

The invention provides a pharmaceutical dosage form comprising an active ingredient combination of nifedipine or nisoldipine and at least one angiotensin II antagonist and/or at least one diuretic and at least one film-forming polymer, characterized in that nifedipine or nisoldipine is located in the core and the angiotensin II antagonist and/or the diuretic is located in a mantle coating around the core.

The invention furthermore provides a pharmaceutical dosage form, characterized in that the film-forming polymer is partially hydrolyzed polyvinyl alcohol.

The invention furthermore provides a pharmaceutical dosage form, characterized in that the film-forming polymer used is a commercially available preparation, a "finished coating" which already comprises further pharmaceutical excipients and is simply dissolved in water.

The invention furthermore provides a pharmaceutical dosage form, characterized in that the film-forming polymer used is OPADRY® II 85F19250 Clear (a polyvinyl alcohol-based finished coating from Colorcon, Inc) of the composition: partially hydrolyzed polyvinyl alcohol, talc, polyethylene glycol (PEG 3350), and polysorbate 80 (commercially available as TWEEN® 80).

The invention furthermore provides a pharmaceutical dosage form comprising an active ingredient combination of nifedipine or nisoldipine and at least one angiotensin II antagonist and at least one film-forming polymer, characterized in that nifedipine or nisoldipine is located in the core and the angiotensin II antagonist is located in a mantle coating around the core.

The invention furthermore provides a pharmaceutical dosage form comprising an active ingredient combination of nifedipine or nisoldipine and at least one diuretic and at least one film-forming polymer, characterized in that nifedipine or nisoldipine is located in the core and the diuretic is located in a mantle coating around the core.

The invention furthermore provides a pharmaceutical dosage form comprising an active ingredient combination of nifedipine or nisoldipine, an angiotensin II antagonist and at least one diuretic and at least one film-forming polymer, characterized in that nifedipine or nisoldipine is located in the core and the angiotensin II antagonist and the diuretic are located in a mantle coating around the core.

The dosage form according to the invention is characterized in that the release of nifedipine or nisoldipine is delayed and the angiotensin II antagonist or the diuretic is released rapidly.

The invention furthermore provides a pharmaceutical dosage form, characterized in that the pharmaceutical dosage form is solid, administered orally and constructed on the basis of an osmotic active ingredient release system.

The invention furthermore provides a pharmaceutical dosage form, characterized in that the active ingredients are present in crystalline or predominantly crystalline form.

The invention furthermore provides a pharmaceutical dosage form, characterized in that the active ingredients are present in micronized form.

The invention furthermore provides a pharmaceutical dosage form, characterized in that the active ingredients are present in fully or partially amorphous form.

The invention furthermore provides a pharmaceutical dosage form, characterized in that nifedipine or nisoldipine are employed in a minimum dose of 5 mg and a maximum dose of 90 mg.

The invention furthermore provides a pharmaceutical dosage form, characterized in that nifedipine is employed in a minimum dose of 10 mg and a maximum dose of 60 mg and nisoldipine is employed in a minimum dose of 5 mg and a maximum dose of 30 mg.

The invention furthermore provides a pharmaceutical dosage form, characterized in that nifedipine is employed in a dose of 20 mg, 30 mg or 60 mg and nisoldipine is employed in a minimum dose of 5 mg and a maximum dose of 30 mg.

The invention furthermore provides a pharmaceutical dosage form, characterized in that nifedipine or nisoldipine are employed in a minimum dose of 10 mg and a maximum dose of 40 mg.

The invention furthermore provides a pharmaceutical dosage form, characterized in that the angiotensin II antagonist is azilsartan, candesartan, losartan, telmisartan, irbesartan, embursartan, eprosartan, valsartan or olmesartan or a prodrug thereof or a pharmaceutically acceptable salt thereof.

The invention furthermore provides a pharmaceutical dosage form, characterized in that the angiotensin II antagonist is candesartan, olmesartan or telmisartan or a prodrug thereof or a pharmaceutically acceptable salt thereof.

The invention furthermore provides a pharmaceutical dosage form, characterized in that the angiotensin II antagonist is candesartan or telmisartan or a prodrug thereof or a pharmaceutically acceptable salt thereof.

The invention furthermore provides a pharmaceutical dosage form, characterized in that the angiotensin II antagonist is candesartan cilexetil.

The invention furthermore provides a pharmaceutical dosage form, characterized in that the angiotensin II antagonist used is candesartan or a prodrug thereof in a dose of 4-16 mg.

The invention furthermore provides a pharmaceutical dosage form, characterized in that the angiotensin II antagonist used is candesartan or a prodrug thereof in a dose of 2-32 mg.

The invention furthermore provides a pharmaceutical dosage form, characterized in that the angiotensin II antagonist used is candesartan or a prodrug thereof in a dose of 4 mg, 8 mg, 16 mg or 32 mg.

The invention furthermore provides a pharmaceutical dosage form, characterized in that the angiotensin II antagonist used is candesartan or a prodrug thereof in a dose of 4-16 mg.

The invention furthermore provides a pharmaceutical dosage form, characterized in that the angiotensin II antagonist used is olmesartan or a prodrug thereof in a dose of 5-40 mg.

The invention furthermore provides a pharmaceutical dosage form, characterized in that olmesartan or a prodrug thereof is used in a dose of 10 to 40 mg.

The invention furthermore provides a pharmaceutical dosage form, characterized in that the angiotensin II antagonist used is telmisartan in a dose of 10 to 80 mg.

The invention furthermore provides a pharmaceutical dosage form, characterized in that telmisartan is used in a dose of 10 to 40 mg.

The invention furthermore provides a pharmaceutical dosage form, characterized in that telmisartan is used in a dose of 20 mg, 40 mg or 80 mg.

The invention furthermore provides a pharmaceutical dosage form, characterized in that lorsartan is used in a dose of 25 to 100 mg.

The invention furthermore provides a pharmaceutical dosage form, characterized in that lorsartan is used in a dose of 40 to 60 mg.

The invention furthermore provides a pharmaceutical dosage form, characterized in that irbesartan is used in a dose of 50 to 500 mg.

The invention furthermore provides a pharmaceutical dosage form, characterized in that irbesartan is used in a dose of 75 to 300 mg.

The invention furthermore provides a pharmaceutical dosage form, characterized in that the diuretic is hydrochlorothiazide, chlorthalidone, mefruside, piretanide or indapamide.

The invention furthermore provides a pharmaceutical dosage form, characterized in that the diuretic is hydrochlorothiazide or chlorthalidone.

The invention furthermore provides a pharmaceutical dosage form consisting of an osmotic single-chamber system.

The invention furthermore provides a pharmaceutical dosage form consisting of an osmotic single-chamber system comprising
  a core, comprising
    5 to 50% of the active ingredient nifedipine or nisoldipine,
    10 to 50% xanthan,
    5 to 40% of a vinylpyrrolidone-vinyl acetate copolymer,
  and also a coat consisting of a water-permeable material which is impermeable for the components of the core and has at least one orifice.

The invention furthermore provides a pharmaceutical dosage form which additionally comprises sodium chloride in the core as an osmotically active additive.

The invention furthermore provides a pharmaceutical dosage form which additionally comprises sodium chloride in the core as an osmotically active additive in an amount of up to 30%, based on the total weight of the ingredients of the inner core.

The invention furthermore provides a pharmaceutical dosage form, characterized in the the coat consists of cellulose acetate or a mixture of cellulose acetate and polyethylene glycol.

The invention furthermore provides a process for preparing an osmotic single-chamber system, characterized in that the components of the core are mixed with one another, granulated and tableted, the resulting core is coated with a coat and the coat is then provided with one or more orifices.

The invention furthermore provides a process for preparing an osmotic single-chamber system, characterized in that a wet granulation is carried out.

The invention furthermore provides a pharmaceutical dosage form consisting of an osmotic two-chamber system.

The invention furthermore provides a pharmaceutical dosage form consisting of an osmotic two-chamber system comprising
  a core having an active ingredient layer, comprising
    5 to 50% of the active ingredient nifedipine or nisoldipine,
    40 to 95% of one or more osmotically active polymers,
  and an osmosis layer, comprising
    40 to 95% of one or more osmotically active polymers,
    5 to 40% of an osmotically active additive,
  and also a coat consisting of a water-permeable material which is impermeable for the components of the core and has at least one orifice.

The invention furthermore provides a pharmaceutical dosage form which additionally comprises sodium chloride in the core as an osmotically active additive.

The invention furthermore provides a pharmaceutical dosage form which comprises in the core in the active ingredient layer polyethylene oxide having a viscosity of 40 to 100 mPa·s (5% strength aqueous solution, 25° C.) as osmotically active polymer and in the core in the osmosis layer polyethylene oxide having a viscosity of 5000 to 8000 mPa·s (1% strength aqueous solution, 25° C.) as osmotically active polymer.

The invention furthermore provides a pharmaceutical dosage form, characterized in that the coat consists of cellulose acetate or a mixture of cellulose acetate and polyethylene glycol.

The invention furthermore provides a process for preparing an osmotic two-chamber system, characterized in that
  the components of the active ingredient layer are mixed and granulated and
  the components of the osmosis layer are mixed and granulated,
  both sets of granules are then compressed on a bilayer tablet press to give a bilayer tablet,
  the resulting inner core is then coated with the coat and
  the coat is, on the active ingredient side, provided with one or more orifices.

The invention furthermore provides a process for preparing an osmotic two-chamber system, characterized in that the components of the active ingredient layer are subjected to dry granulation.

The invention furthermore provides a medicament comprising a pharmaceutical dosage form.

The invention furthermore provides the use of a pharmaceutical dosage form for the prophylaxis, secondary prophylaxis and/or treatment of disorders.

The invention furthermore provides the use of a pharmaceutical dosage form for preparing a medicament for the prophylaxis, secondary prophylaxis and/or treatment of disorders.

The invention furthermore provides the use for the prophylaxis, secondary prophylaxis and/or treatment of cardiovascular disorders.

The invention furthermore provides the use for the prophylaxis, secondary prophylaxis and/or treatment of hypertension.

The invention furthermore provides the use of nifedipine or nisoldipine and an angiotensin II antagonist and/or a diuretic for preparing a pharmaceutical dosage form.

The invention furthermore provides the pharmaceutical dosage form into which, in addition to nifedipine or nisoldipine and the angiotensin II antagonist, a further antihypertensive active ingredient is incorporated.

The invention furthermore provides the pharmaceutical dosage form into which, in addition to nifedipine or nisoldipine and the angiotensin II antagonist, a diuretic is incorporated.

The invention furthermore provides the pharmaceutical dosage form where hydrochlorothiazide is employed.

The invention furthermore provides a process for the prophylaxis, secondary prophylaxis and/or treatment of cardiovascular disorders by administering a solid pharmaceutical dosage form which is based on active ingredient release systems, can be administered orally and comprises a nifedipine or nisoldipine/angiotensin II antagonist combination.

The core of the pharmaceutical dosage form according to the invention for its part may be a delayed-release tablet, a mantle tablet, a coated tablet, a coated mantle tablet, a delayed-release capsule or an osmotic active ingredient release system, coated with the mantle coating according to the invention comprising at least one angiotensin II antagonist and/or at least one diuretic. The core is preferably an osmotic active ingredient release system.

Accordingly, the invention preferably provides a pharmaceutical dosage form comprising an active ingredient combination of nifedipine or nisoldipine and at least one angiotensin II antagonist and/or at least one diuretic, characterized in that nifedipine or nisoldipine is located in the core of an osmotic active ingredient release system and the angiotensin II antagonist and/or the diuretic is located in a mantle coating on top of the osmotic active ingredient release system.

The invention furthermore provides a pharmaceutical dosage form comprising an active ingredient combination of nifedipine or nisoldipine and at least one angiotensin II antagonist and/or at least one diuretic, characterized in that nifedipine or nisoldipine is located in the core and is released in a controlled (modified) manner and the angiotensin II antagonist and/or the diuretic is located in a mantle coating and is released rapidly in the body.

Preferred for use as angiotensin II antagonists are azilsartan, candesartan, losartan, telmisartan, irbesartan, embursartan, eprosartan, valsartan or olmesartan, particularly preferably candesartan, olmesartan or telmisartan, very particularly preferably candesartan or telmisartan, or prodrugs thereof. The term "prodrugs" includes compounds which may themselves be biologically active or inactive but are converted (for example by metabolism or hydrolysis) during their residence time in the body into the compounds used according to the invention. A prodrug of candesartan is, for example, candesartan cilexetil. This and further examples of suitable prodrugs are disclosed in *J. Med. Chem.* 1993 Aug. 6; 36(16):2343-9. A prodrug of olmesartan is, for example, olmesartan medoxomil. The sartans mentioned can also be present in the form of pharmaceutically suitable salts, for example losartan potassium and eprosartan mesylate. In a particularly preferred embodiment, use is made of the angiotensin II antagonist candesartan cilexetil.

Preferred diuretics which may be mentioned are carboanhydrase inhibitors such as, for example, acetazolamide, dichlorphenamide and methazolamide, or loop diuretics such as, for example, furosemide, torasemide, bumetanide, etacrynic acid and piretanide, or potassium-sparing diuretics such as, for example, amiloride and triamterene, or aldosterone antagonists such as, for example, spironolactone, potassium canrenoate and eplerenone, or thiazide diuretics and other sulphonamide diuretics such as, for example, hydrochlorothiazide, chlorthalidone, xipamide, metolazone, mefruside and indapamide. Hydrochlorothiazide, chlorthalidone, mefrusid, piretanide and indapamide may be mentioned as being particularly preferred. Very particular preference is given to using hydrochlorothiazide or chlorthalidone.

The dosage form according to the invention preferably comprises nifedipine or nisoldipine in dosages of from 5 to 90 mg, in the case of nifedipine preferably in dosages of from 10 to 60 mg, particularly preferably in dosages of 20, 30 or 60 mg, in the case of nisoldipine preferably in dosages of from 5 to 30 mg, and at least one angiotensin II antagonist in dosages of from 2 to 500 mg, preferably candesartan, particularly preferably candesartan cilexetil in dosages of from 2 to 40 mg, preferably from 4 to 32 mg, particularly preferably in dosages of 4, 8, 16 or 32 mg, also preferably olmesartan, particularly preferably olmesartan medoxomil in a dosage of from 5 to 40 mg, preferably from 10 to 40 mg, also preferably telmisartan in a dosage of from 10 to 80 mg, particularly preferably in a dosage of 20, 40 or 80 mg, also preferably losartan in a dosage of from 25 to 100 mg, preferably from 40 to 60 mg, also preferably azilsartan in a dosage of from 20 to 80 mg, also preferably valsartan in a dosage of from 40 to 320 mg, preferably from 80 to 160 mg, also preferably irbesartan in a dosage of from 50 to 500 mg, preferably from 75 to 300 mg, also preferably eprosartan in a dosage of from 300 to 600 mg, and/or at least one diuretic in dosages of from 0.5 to 500 mg, preferably hydrochlorothiazide (HCT, HCTZ) in dosages of from 12.5 to 25 mg, also preferably chlorthalidone in dosages of from 12.5 mg to 50 mg, also preferably metolazone in dosages of from 5 to 10 mg, also preferably spironolactone in dosages of from 25 to 100 mg, also preferably furosemide in dosages of from 20 to 80 mg, also preferably mefruside in a dosage of 12.5 mg, also preferably piretanide in dosages of from 3 to 6 mg, also preferably indapamide in dosages of from 0.5 to 5 mg.

Particularly preferred dosage combinations are all 87 possible combinations of nifedipine in doses of 20 mg, 30 mg and 60 mg with candesartan cilexetil in doses of 4 mg, 8 mg, 16 mg and 32 mg and/or a diuretic selected from hydrochlorothiazide in doses of 12.5 mg and 25 mg and chlorthalidone in doses of 12.5 mg, 25 mg and 50 mg.

These possible combinations are illustrated in the tables below (all amounts in mg):

TABLE a

Combinations of two active ingredients

| No. | Nifedipine | Candesartan cilexetil | Hydrochlorothiazide | Chorthalidone |
|---|---|---|---|---|
| 1 | 20 | 4 | | |
| 2 | 20 | 8 | | |
| 3 | 20 | 16 | | |
| 4 | 20 | 32 | | |
| 5 | 20 | | 12.5 | |
| 6 | 20 | | 25 | |
| 7 | 20 | | | 12.5 |
| 8 | 20 | | | 25 |
| 9 | 20 | | | 50 |
| 10 | 30 | 4 | | |

TABLE a-continued

Combinations of two active ingredients

| No. | Nifedipine | Candesartan cilexetil | Hydrochlorothiazide | Chorthalidone |
|---|---|---|---|---|
| 11 | 30 | 8 | | |
| 12 | 30 | 16 | | |
| 13 | 30 | 32 | | |
| 14 | 30 | | 12.5 | |
| 15 | 30 | | 25 | |
| 16 | 30 | | | 12.5 |
| 17 | 30 | | | 25 |
| 18 | 30 | | | 50 |
| 19 | 60 | 4 | | |
| 20 | 60 | 8 | | |
| 21 | 60 | 16 | | |
| 22 | 60 | 32 | | |
| 23 | 60 | | 12.5 | |
| 24 | 60 | | 25 | |
| 25 | 60 | | | 12.5 |
| 26 | 60 | | | 25 |
| 27 | 60 | | | 50 |

TABLE b

Combinations of three active ingredients

| No. | Nifedipine | Candesartan cilexetil | Hydrochlorothiazide | Chorthalidone |
|---|---|---|---|---|
| 28 | 20 | 4 | 12.5 | |
| 29 | 20 | 4 | 25 | |
| 30 | 20 | 4 | | 12.5 |
| 31 | 20 | 4 | | 25 |
| 32 | 20 | 4 | | 50 |
| 33 | 20 | 8 | 12.5 | |
| 34 | 20 | 8 | 25 | |
| 35 | 20 | 8 | | 12.5 |
| 36 | 20 | 8 | | 25 |
| 37 | 20 | 8 | | 50 |
| 38 | 20 | 16 | 12.5 | |
| 39 | 20 | 16 | 25 | |
| 40 | 20 | 16 | | 12.5 |
| 41 | 20 | 16 | | 25 |
| 42 | 20 | 16 | | 50 |
| 43 | 20 | 32 | 12.5 | |
| 44 | 20 | 32 | 25 | |
| 45 | 20 | 32 | | 12.5 |
| 46 | 20 | 32 | | 25 |
| 47 | 20 | 32 | | 50 |
| 48 | 30 | 4 | 12.5 | |
| 49 | 30 | 4 | 25 | |
| 50 | 30 | 4 | | 12.5 |
| 51 | 30 | 4 | | 25 |
| 52 | 30 | 4 | | 50 |
| 53 | 30 | 8 | 12.5 | |
| 54 | 30 | 8 | 25 | |
| 55 | 30 | 8 | | 12.5 |
| 56 | 30 | 8 | | 25 |
| 57 | 30 | 8 | | 50 |
| 58 | 30 | 16 | 12.5 | |
| 59 | 30 | 16 | 25 | |
| 60 | 30 | 16 | | 12.5 |
| 61 | 30 | 16 | | 25 |
| 62 | 30 | 16 | | 50 |
| 63 | 30 | 32 | 12.5 | |
| 64 | 30 | 32 | 25 | |
| 65 | 30 | 32 | | 12.5 |
| 66 | 30 | 32 | | 25 |
| 67 | 30 | 32 | | 50 |
| 68 | 60 | 4 | 12.5 | |
| 69 | 60 | 4 | 25 | |
| 70 | 60 | 4 | | 12.5 |
| 71 | 60 | 4 | | 25 |
| 72 | 60 | 4 | | 50 |
| 73 | 60 | 8 | 12.5 | |
| 74 | 60 | 8 | 25 | |

TABLE b-continued

Combinations of three active ingredients

| No. | Nifedipine | Candesartan cilexetil | Hydrochlorothiazide | Chorthalidone |
|---|---|---|---|---|
| 75 | 60 | 8 | | 12.5 |
| 76 | 60 | 8 | | 25 |
| 77 | 60 | 8 | | 50 |
| 78 | 60 | 16 | 12.5 | |
| 79 | 60 | 16 | 25 | |
| 80 | 60 | 16 | | 12.5 |
| 81 | 60 | 16 | | 25 |
| 82 | 60 | 16 | | 50 |
| 83 | 60 | 32 | 12.5 | |
| 84 | 60 | 32 | 25 | |
| 85 | 60 | 32 | | 12.5 |
| 86 | 60 | 32 | | 25 |
| 87 | 60 | 32 | | 50 |

Other particularly preferred dosage combinations are all possible two-component and three-component combinations of nifedipine in doses of 20 mg, 30 mg and 60 mg with telmisartan in doses of 20 mg, 40 mg, 80 mg and/or a diuretic selected from hydrochlorothiazide in doses of 12.5 mg and 25 mg and chlorthalidone in doses of 12.5 mg, 25 and 50 mg.

Preferably, the complete amount of nifedipine or nisoldipine active ingredient is located in the core, preferably in the core of the osmotic release system, and the complete amount of angiotensin II antagonist and/or diuretic active ingredient is located in the mantle coating. In embodiments comprising an angiotensin II antagonist and a diuretic in the mantle coating, the angiotensin II antagonist and the diuretic may be located in the same layer of the mantle coating or in separate layers, applied in succession, of the mantle coating.

It may be necessary where appropriate to deviate from the stated amounts, in particular as a function of the body weight and the type of the administration route, of the individual behaviour in relation to the medicament, the nature of its formulation and the time or interval over which administration takes place. Thus, in some cases it may be adequate to manage with less than the abovementioned minimum amount, while in other cases the upper limit mentioned has to be exceeded.

The invention furthermore provides solid pharmaceutical dosage forms which are administered orally and comprise an active ingredient combination to be administered once every day, of nifedipine or nisoldipine with an angiotensin II antagonist and/or a diuretic, based on osmotic release systems, characterized in that at least 85% of the nifedipine or nisoldipine (based on the declared total amount of the active ingredient in question) are released over a period of at least 4 and at most 24 hours, preferably 5 to 17% of the nifedipine or nisoldipine within 4 hours and 43 to 80% of the nifedipine or nisoldipine within 12 hours according to the USP release method using apparatus 2 (paddle) at 100 revolutions per minute in 900 ml of phosphate buffer pH 6.8 with addition of 1% sodium lauryl sulphate at 37° C. and at least 70% of the angiotensin II antagonist and/or the diuretic (based on the declared total amount of the active ingredient in question) are released within 30 minutes according to the USP release method using apparatus 2 (paddle) at 75 revolutions per minute in 1000 ml of a suitable medium, for example phosphate buffer at 37° C.

The invention furthermore provides solid pharmaceutical dosage forms which are administered orally and comprise an active ingredient combination to be administered once every day, of nifedipine or nisoldipine with an angiotensin II antagonist and/or a diuretic, based on osmotic release systems, characterized in that at least 85% of the nifedipine or nisoldipine (based on the declared total amount of the active ingredient in question) are released over a period of at least 4 and at most 24 hours, preferably 5 to 17% of the nifedipine or nisoldipine within 4 hours and 43 to 80%, particularly preferably 45 to 75%, of the nifedipine or nisoldipine within 12 hours, and also at least 60%, preferably at least 70%, particularly preferably at least 80%, of the angiotensin II antagonist and/or the diuretic (based on the declared total amount of the active ingredient in question) are released within 30 minutes according to the USP release method using apparatus 2 (paddle) at 75 revolutions per minute in 900 ml of a suitable medium, for example 0.1 N hydrochloric acid (pH 1.0) with addition of 1.0% sodium lauryl sulphate or phosphate buffer pH 6.8 with addition of 1.0% sodium lauryl sulphate at 37° C.

It is known to the person skilled in the art that the conditions of the release test have to be adapted to the solubilities of the active ingredient. For formulations comprising nifedipine and candesartan cilexetil, the test for in-vitro dissolution is preferably carried out, for example, for both active ingredients simultaneously according to the USP release method using apparatus 2 (paddle), at 75 revolutions in 900 ml of a suitable medium at 37° C., where the suitable medium is selected from 0.1 N hydrochloric acid (pH 1.0), 0.01 N hydrochloric acid (pH 2.0), acetate buffer pH 4.5, phosphate buffer pH 6.5, phosphate buffer pH 6.8 and phosphate buffer pH 8.0, in each case with addition of 0.6-1.0% sodium lauryl sulphate or 0.6-1.0% polysorbate 20 (Tween 20). Particular preference is given to 0.1 N hydrochloric acid (pH 1.0) with addition of 1.0% sodium lauryl sulphate.

The invention furthermore provides solid pharmaceutical dosage forms which are administered orally and comprise an active ingredient combination to be administered once every day, of nifedipine with candesartan cilexetil and, if appropriate, a diuretic, based on osmotic release systems, characterized in that at least 85% of the nifedipine (based on the declared total amount of nifedipine) are released over a period of 24 hours, 5 to 17% of the nifedipine within 4 hours and 45 to 75% of the nifedipine within 12 hours, and also at least 70% of the candesartan cilexetil (based on the declared total amount of candesartan cilexetil) are released within 30 minutes according to the USP release method using apparatus 2 (paddle) at 75 revolutions per minute in 900 ml of 0.1 N hydrochloric acid (pH 1.0) with addition of 1.0% sodium lauryl sulphate at 37° C.

The invention furthermore provides solid pharmaceutical dosage forms which are administered orally and comprise an active ingredient combination to be administered once every day, of nifedipine with telmisartan and, if appropriate, a diuretic, based on osmotic release systems, characterized in that at least 85% of the nifedipine (based on the declared total amount of nifedipine) are released over a period of 24 hours, 5 to 17% of the nifedipine within 4 hours and 43 to 80% of the nifedipine within 12 hours, and also at least 60% of the telmisartan (based on the declared total amount of telmisartan) are released within 30 minutes according to the USP release method using apparatus 2 (paddle) at 75 revolutions per minute in 900 ml of acetate buffer pH 4.5 with addition of 0.6% sodium lauryl sulphate at 37° C.

The invention furthermore provides solid pharmaceutical dosage forms which are administered orally and comprise an active ingredient combination to be administered once every day, of nifedipine or nisoldipine with an angiotensin II antagonist and/or a diuretic, based on osmotic release systems, characterized in that the release profile of nifedipine differs by less than 30 minutes, preferably less than 15 minutes, particularly preferably by less than 5 minutes, from the release profile of nifedipine in ADALAT® GITS (a gastrointestinal therapeutic system) formulations of the same dosage and the release profile of the angiotensin II antagonist and/or the diuretic by less than 10 minutes, preferably less than 5 minutes, from the release profile of the angiotensin II antagonist in the marketed formulation of the same doses corresponding to the active ingredient, such as, for example, candesartan cilexetil in ATACAND® or BLOPRESS®, telmisartan in KINZALMONO® or MICARDIS®, or hydrochlorothiazide in ESIDRIX®.

The active ingredients in the pharmaceutical dosage forms according to the invention can be present in crystalline form or in non-crystalline amorphous form or in mixtures having crystalline and amorphous active ingredient portions. Some active ingredients may be present in a plurality of crystal modifications. In principle, the pharmaceutical dosage forms according to the invention may comprise the active ingredients in all possible crystal forms. It is known, for example, that candesartan cilexetil occurs in modification I or type C (cf. EP 0 459 136 B1). Furthermore, it is known that there are other crystal modifications of candesartan cilexetil (cf., for example, WO 2008/035360 A). Candesartan cilexetil is preferably employed in crystal modification I. Telmisartan, too, is known to have a polymorphic crystal modification B (cf. WO 00/43370 A).

To achieve a distribution of the active ingredient which is as uniform as possible, the active ingredient is employed for the dosage forms according to the invention in a particle size which is as small as possible. The person skilled in the art is familiar with methods for reducing the particle size. From among these, preference is given in particular to fine grinding using an air jet mill (micronization). Using this grinding process, it is typically possible to achieve particle size distributions characterized by an $X_{50}$ value of 10 μm or less and by an $X_{90}$ value of 30 μm or less.

If the dosage forms according to the invention comprise the active ingredients in crystalline form, they are, in a preferred embodiment of the present invention, employed in micronized form, preferably having an average particle diameter of less than 10 μm, preferably less than 5 μm, particularly preferably less than 3 μm. Here, nifedipine or nisoldipine preferably has an average particle size $X_{50}$ of from 2 to 6 μm and an $X_{90}$ value (90% portion) of less than 12 μm. Candesartan cilexetil preferably has an average particle size $X_{50}$ of from 0.5 to 8 μm, preferably from 1 to 5 μm, and an $X_{90}$ value (90% portion) of less than 20 μm, preferably less than 10 μm. The $X_{50}$ and $X_{90}$ values always refer to the particle size distribution, determined by laser diffractometry and stated as volume distribution.

Both osmotic single-chamber systems (elementary osmotic pump) and two-chamber systems (push-pull systems) are suitable for the osmotic active ingredient release system.

The coat of the osmotic active ingredient release system consists, in both the single-chamber system and in the two-chamber system, of a water-permeable material which is impermeable for the components of the inner core. Such coat materials are known in principle and described for example in EP 024 793 B1, pages 3-4, the disclosure of which is incorporated herein by reference. Preferably employed as coat material according to the invention are cellulose acetate or mixtures of cellulose acetate and polyethylene glycol.

In the osmotic single-chamber system, the inner core comprises preferably from 5 to 50% nifedipine or nisoldipine, from 10 to 50% xanthan and from 5 to 40% of a vinylpyrrolidone-vinyl acetate copolymer, where, if appropriate, the difference to 100% is made up by one or more additional components selected from the group consisting of further hydrophilic swellable polymers, osmotically active additives and pharmaceutically customary excipients. The sum of the inner core ingredients is 100%, and the %-data are in each case based on the total mass of the inner core.

The osmotic single-chamber system comprises as one of the essential ingredients of the inner core the hydrophilic water-swellable polymer xanthan. This is an anionic heteropolysaccharide which is obtainable commercially, for example under the name Rhodigel® (produced by Rhodia). It is present in an amount of from 10 to 50%, preferably from 20 to 40%, based on the total mass of the inner core ingredients.

A further essential ingredient of the inner core is the vinylpyrrolidone-vinyl acetate copolymer. This copolymer is known per se and can be produced with any desired monomer mixing ratios. The commercially available Kollidon® VA64 (produced by BASF) which is preferably used is, for example, a 60:40 copolymer. It generally has a weight average molecular weight Mw, determined by light-scattering measurements, of about 45 000 to about 70 000. The amount of the vinylpyrrolidone-vinyl acetate copolymer in the inner core is 5 to 40%, preferably 15 to 25%, based on the total mass of the inner core ingredients.

Hydrophilic swellable polymers which are additionally present where appropriate in the inner core are, for example, hydroxypropylcellulose, hydroxypropylmethylcellulose, sodium carboxymethylcellulose, sodium carboxymethyl starch, polyacrylic acids and salts thereof.

Osmotically active additives which are additionally present where appropriate in the inner core are, for example, all water-soluble substances acceptable for use in pharmacy, such as, for example, the water-soluble excipients mentioned in pharmacopeias or in "Hager" and "Remington Pharmaceutical Science". It is possible in particular to use water-soluble salts of inorganic or organic acids or nonionic organic substances with high solubility in water, such as, for example, carbohydrates, especially sugars, sugar alcohols or amino acids. For example, the osmotically active additives can be selected from inorganic salts such as chlorides, sulphates, carbonates and bicarbonates of alkali metals or alkaline earth metals, such as lithium, sodium, potassium, magnesium, calcium, and phosphates, hydrogen phosphates or dihydrogen phosphates, acetates, succinates, benzoates, citrates or ascorbates thereof. It is furthermore possible to use pentoses such as arabinose, ribose or xylose, hexoses such as glucose, fructose, galactose or mannose, disaccharides such as sucrose, maltose or lactose or trisaccharides such as raffinose. The water-soluble amino acids include glycine, leucine, alanine or methionine. Sodium chloride is particularly preferably used according to the invention. The osmotically active additives are preferably present in an amount of up to 30% based on the total mass of the inner core ingredients.

Pharmaceutically usual excipients which are additionally present where appropriate in the inner core are, for example, buffer substances such as sodium bicarbonate, binders such as hydroxypropylcellulose, hydroxypropylmethylcellulose or polyvinylpyrrolidone, lubricants such as magnesium stearate, wetting agents such as sodium lauryl sulphate or flow regulators such as colloidal silicon dioxide and stabilizers such as antioxidants.

To prepare the osmotic single-chamber system, it is possible, for example, to mix the components of the inner core comprising nifedipine or nisoldipine, to subject them, if appropriate, to wet or dry, preferably wet, granulation and then to tabletting, and to provide the resulting inner core with the coat, which is provided with one or more orifices.

In the osmotic two-chamber system, the inner core consists of two layers, one active ingredient layer and one osmosis layer. An osmotic two-chamber system of this type is described in detail for example in DE 34 17 113 C 2, the disclosure of which is incorporated herein by reference.

The active ingredient layer preferably comprises from 5 to 50% nifedipine or nisoldipine, preferably from 10 to 45%, furthermore preferably from 10 to 40%, furthermore preferably from 10 to 30%, furthermore particularly preferably from 15 to 25%, especially preferably from 18 to 22%, very particularly preferably 20%, and from 40 to 95%, preferably from 50 to 85%, furthermore preferably from 55 to 85%, furthermore preferably from 60 to 85%, furthermore very particularly preferably from 65 to 85%, especially preferably from 70 to 80%, of one or more osmotically active polymers, preferably polyethylene oxide of medium viscosity (40 to 100 mPa·s; 5% strength aqueous solution, 25° C.), and the osmosis layer preferably comprises from 40 to 90%, preferably from 50 to 80%, furthermore preferably from 55 to 75%, furthermore preferably from 55 to 70%, especially from 60 to 67%, of one or more osmotically active polymers, preferably polyethylene oxide of high viscosity (5000 to 8000 mPa·s; 1% strength aqueous solution, 25° C.), and from 5 to 40%, preferably from 10 to 40%, furthermore preferably from 15 to 40%, furthermore preferably from 20 to 40%, especially preferably from 20 to 35%, of an osmotically active additive, where the difference to 100% in the individual layers independently of one another is in each case made up by one or more additional ingredients in the form of pharmaceutically customary auxiliaries. The % data are in each case based on the total mass of the particular inner core layer.

The osmotically active additives used in the inner core of the osmotic two-chamber system may furthermore be the same as in the case of the single-chamber system described above. Sodium chloride is preferred in this connection.

The pharmaceutically customary excipients used in the inner core of the osmotic two-chamber system may be the same as in the case of the single-chamber system described above. Preference is given in this connection to binders such as hydroxypropylcellulose, hydroxypropylmethylcellulose or polyvinylpyrrolidone, lubricants such as magnesium stearate, wetting agents such as sodium lauryl sulphate or flow regulators such as finely divided silicon dioxide, a coloring pigment such as iron oxide in one of the two layers to differentiate active ingredient layer and osmosis layer, and stabilizers/antioxidants in the active ingredient layer.

To prepare the osmotic two-chamber system, it is possible, for example, to mix the components of the active ingredient layer comprising nifedipine or nisoldipine and to subject them to wet or dry, preferably dry, granulation, to mix and granulate the components of the osmosis layer and then to compress both sets of granules on a bilayer tablet press to give a bilayer tablet. The resulting inner core is then provided with a coat. The coat is, on the active ingredient side, provided with one or more orifices. Alternatively, the provision of the one or more orifices in this process step may be dispensed with. In this case, only after the coating with one or more further mantle coatings has been carried out, both sides of the tablet are each provided with an orifice extending in each case from the outside to the inner core, i.e. streching across the mantle coatings and the coat.

In a preferred embodiment of the present invention, both the components of the active ingredient layer and the components of the osmosis layer are each subjected to granulation, in particular by means of roller granulation, in the production of the osmotic two-chamber system.

Preference is given according to the invention, because of the physicochemical properties of the active ingredient combination, to osmotic two-chamber systems (push-pull systems) in which the active ingredient layer and osmosis layer are separated, by way of example and advantageously formulated as 2-layer tablet. Here, the advantages compared to osmotic single-chamber systems are the more uniform release rate over a longer period of time, and also the possibility to reduce the systemically required excess of active ingredient.

The mantle coating of the dosage forms according to the invention comprises at least one angiotensin II antagonist and/or at least one diuretic and at least one film-forming polymer. The film-forming polymer may be chosen such that it is suitable for the rapid release of active ingredients. In embodiments comprising an angiotensin II antagonist and a diuretic in the mantle coating, the angiotensin II antagonist and the diuretic may be located in the same coating layer or in separate coating layers, applied in succession.

Suitable for use as film-forming polymers are cellulose derivatives, synthetic polymers and mixtures thereof.

Cellulose derivatives that may be mentioned are methylcellulose (MC), hydroxymethylpropylcellulose (HPMC), hydroxypropylcellulose (HPC), carboxymethylcellulose-sodium (Na-CMC), hydroxyethylcellulose (HEC) and mixtures thereof.

Synthetic polymers that may be mentioned are polyvinylpyrrolidone (povidone, PVP), vinylpyrrolidone-vinyl acetate copolymer (copovidone), polyvinyl alcohol (PVA), polyvinyl acetate (PVAc), partially hydrolyzed polyvinyl alcohol, polyvinyl alcohol-polyethylene glycol copolymers (PVA-co-PEG) and mixtures thereof.

Preferred film-formers are polyvinyl alcohol (PVA), polyvinyl acetate (PVAc), partially hydrolyzed polyvinyl alcohol, polyvinyl alcohol-polyethylene glycol copolymers (PVA-PEG copolymer) and mixtures thereof.

A preferred film-former is in particular partially hydrolyzed polyvinyl alcohol.

Preference is furthermore given in particular to the commercially available preparations below, "finished coatings" which already comprise further pharmaceutical excipients and are simply dissolved in water.

Kollicoat IR white (BASF PVA-co-PEG-based finished coating with white pigment), composition: Kollicoat IR (PVA-co-PEG), Kollidon VA64 (copovidone), kaolin, sodium lauryl sulphate, titanium dioxide.

Sepifilm IR Colorless (SEPPIC PVA-co-PEG-based finished coating without pigments), composition: Kollicoat IR (PVA-co-PEG), polydextrose, kaolin, polyethylene glycol (PEG 400).

Opadry II 85F19250 Clear (Colorcon PVA-based finished coating), composition: partially hydrolyzed polyvinyl alcohol, talc, polyethylene glycol (PEG 3350), polysorbate 80 (Tween 80). This finished coating is particularly preferred.

Opadry II 85F28393 (Colorcon PVA-based finished coating), composition: partially hydrolyzed polyvinyl alcohol, talc, polyethylene glycol (PEG 3350), titanium dioxide.

The mantle coating can also be prepared from the individual components, for example from the following commercially available preparations: BASF Kollicoat IR (PVA-co-PEG), BASF Kollidon VA64 (copovidone), Merck Emprove (PVA).

The mantle coating may comprise further excipients such as, for example, wetting agents (for example sodium lauryl sulphate, quaternary ammonium compounds, lecithin (in particular soya lecithin), polysorbates (in particular Polysorbat 80, synonym Tween 80)), pigments (for example titanium dioxide, talc), colour pigments (for example iron oxide red, yellow or black or mixtures thereof), release agents (for example kaolin, talc, finely divided silica, magnesium stearate, glycerol monostearate), and/or plasticizers (for example polyethylene glycol (in particular polyethylene glycol 400, polyethylene glycol 3350), polypropylene glycol, propylene glycol, glycerol, triacetin, triethyl citrate).

In the mantle coating, the proportion of angiotensin II antagonist, if appropriate together with the proportion of diuretic, is from 10 to 50%, preferably from 15 to 40%, preferably from 10 to 40%, particularly preferably from 20 to 40%, furthermore preferably from 20 to 45%, particularly preferably from 25 to 45%, particularly preferably from 30 to 45%, very particularly preferably 20, 30, 33, 40% or 45%, the proportion of film-forming polymer is from 20 to 75%, preferably from 25 to 60%, particularly preferably about 30 to 45%, the proportion of pigment is from 0 to 20%, the proportion of wetting agent is from 0 to 3%, preferably from 1 to 2%, based on the dry weight of the mantle coating. When finished coatings are used, the proportion of angiotensin II antagonist, if appropriate together with the proportion of diuretic, is from 10 to 50%, preferably from 15 to 40%, preferably from 10 to 40%, particularly preferably from 20 to 40%, furthermore preferably from 20 to 45%, particularly preferably from 25 to 45%, particularly preferably from 30 to 45%, very particularly preferably 20, 30, 33, 40% or 45%, particularly preferably 40%, and the proportion of finished coating is from 50 to 90%, preferably from 50 to 80%, preferably from 50 to 75%, preferably from 55 to 70%, preferably 60, 67, 70 or 80%, particularly preferably 60%. Here, the percentages for the mantle coating refer to the active ingredient coating without any colouring coating that may be present.

The proportion of mantle coating without any colouring coating that may be present in the dosage form according to the invention is from 5 to 100%, preferably from 5 to 80%, particularly preferably from 10 to 50%, furthermore particularly preferably, for example, about more than 10%, 15%, 20%, 30%, 40% or 50%, based on the core weight.

Based on the total weight of the dosage form, the proportion of mantle coating without any colouring coating that may be present in the dosage form according to the invention is from 4 to 50%, preferably from 5 to 45%, particularly preferably from 9 to 33%, furthermore particularly preferably, for example, about more than 10%, 15%, 20%, 25%, 30% or 33%.

The weight of the mantle coating in the dosage form according to the invention is generally from 10 to 300 mg, preferably from 20 to 300 mg, preferably from 25 to 250 mg, particularly preferably from 50 to 200 mg, furthermore particularly preferably from 100 mg to 150 mg. If only one active ingredient is present in the active ingredient layer, the weight of the mantle coating in the dosage form according to the invention is from 10 to 300 mg, preferably from 10 to 250 mg, preferably from 10 to 150 mg, particularly preferably from 10 to 100 mg, furthermore particularly preferably from 10 mg to 80 mg. If two active ingredients are present in the active ingredient layer, the weight of the mantle coating in the dosage form according to the invention is from 10 to 300 mg, preferably from 20 to 250 mg, preferably from 30 to 200 mg, particularly preferably from 40 to 200 mg, furthermore particularly preferably from 40 mg to 150 mg. Here, the weight of the mantle coating comprises only that of the active ingredient coating, without any colouring coating that may be present.

The thickness of the mantle coating is from 25 to 1500 µm, preferably from 50 to 1500 µm, particularly preferably from 50 to 1200 µm, furthermore particularly preferably from 75 to 1200 µm, very particularly preferably from 100 to 1000 µm, furthermore particularly preferably more than 25 µm, 50 µm, 75 µm, 100 µm, 150 µm, 200 µm, 250 µm.

The dosage form according to the invention meets the pharmacopoeia requirements of content uniformity (for example according to USP 31, Uniformity of dosage units). Here, the acceptance value is less than 15% and the standard deviation in percent of the angiotensin II antagonist and/or the diuretic content in the mantle coating is less than 6.25%, preferably less than 6%, particularly preferably less than 5% for n=10 individual doses, or less than 7.5%, preferably less than 6%, particularly preferably less than 5% for n=10 individual doses. Here, the average content of angiotensin II antagonist and/or diuretic in the mantle coating, calculated from the n=10 oder n=30 individual contents determined, is from 95 to 105%, preferably from 97 to 103%, particularly preferably from 98.5 to 101.5% based on the specified content of the tablets.

In the abrasion test (for example according to USP 31 <1216> Tablet Friability), the dosage form according to the invention shows a very low abrasion of less than 0.5%, preferably less than 0.1%, particularly preferably less than 0.01%, or even no measurable abrasion, based on the weight of the dosage form.

When tested for fracture resistance using a suitable instrument for testing tablets (for example Schleuniger Type 6D or Type 8M, Dr. Schleuniger Pharmatron AG, Solothurn, Switzerland), the dosage form according to the invention shows a fracture resistance of greater than 200 N, preferably greater than 300 N. In a particularly preferred embodiment, during the test for fracture resistance there is neither breaking nor flaking-off of the mantle coating, but at most a slight plastic deformation, up to 449 N.

In the disintegration test (for example according to USP 31 <701> Disintegration), using purified water as medium at 37° C., the mantle coating of the dosage form according to the invention can be detached completely from the core within a period of 40 minutes, preferably within 25 minutes, particularly preferably within 10 minutes.

In the test for in-vitro dissolution, the dosage form according to the invention releases at least 85% of the nifedipine or nisoldipine (based on the declared total amount of the active ingredient in question) over a period of at least 4 and at most 24 hours, preferably from 5 to 17% of the nifedipine or nisoldipine within 4 hours and from 43 to 80%, particularly preferably from 45 to 75% of the nifedipine or nisoldipine within 12 hours. Moreover, in the test for in-vitro dissolution, the dosage form according to the invention releases at least 60%, preferably 70%, particularly preferably at least 80% of the angiotensin II antagonist and/or the diuretic (based on the declared total amount of the active ingredient in question) over a period of 30 minutes. The test for in-vitro dissolution is carried out according to the USP release method using apparatus 2 (paddle), at 50 to 100 revolutions, preferably 75 or 100 revolutions, in from 900 to 1000 ml of a suitable medium at 37° C. Depending on the solubility of the active ingredients, the suitable medium may be selected, for example, from the group consisting of 0.1 N hydrochloric acid (pH 1.0), 0.01 N hydrochloric acid (pH 2.0), acetate buffer pH 4.5, phosphate buffer pH 4.5, phosphate buffer pH 6.8 and phosphate buffer pH 8.0 with 0-1% sodium lauryl sulphate or 0-1% polysorbate 20 (Tween 20), preferably 0.4-1.0% sodium lauryl sulphate, added. The test for in-vitro dissolution can be carried out simultaneously in the same medium for all active ingredients present in a formulation, or independently in different media for the individual active ingredients.

The present invention furthermore provides a process for preparing a dosage form according to the invention comprising a core, preferably an osmotic active ingredient release system as core, and a mantle layer, where, to apply the mantle coating, the cores, for example 800 g, are added to a drum coater having a nominal capacity of 1 kg feed material, and an aqueous coating suspension, for example 1600 g, comprising at least one angiotensin II antagonist and/or at least one diuretic, at least one film-forming polymer and, if appropriate, further auxiliaries, is sprayed on. The temperature of the incoming air is from 40 to 70° C., preferably from 55 bis 65° C., particularly preferably 60° C., for example at an amount of incoming air of about 120 m³/h and a drum speed of from 10 to 18 rpm, preferably from 12 to 15 rpm. The spray nozzle used may, for example, be a circular jet nozzle having a diameter of from 0.8 to 1.2 mm or a flat jet nozzle operated at an atomizer pressure of from 1.6 to 2.2 bar. An initial spray rate of, for example, 4 g/min can be increased during the spraying process continuously or in discrete steps, for example every 10 to 30 minutes in steps of, for example, in each case 1 g/min or of in each case 10% of the actual spray rate, to up to 18 g/min. After the spraying process has ended, for example after 180 to 240 minutes, the tablets can, without any spraying, be polished, for example for 5 to 60 minutes, preferably 10 to 30 minutes, or until completed cooling to room temperature in the drum with discontinuous or continuous rotation of the drum, preferably continuous rotation at a drum speed of from 6 to 15 rpm. For larger or smaller drum coaters, the process parameters may be adapted appropriately. Suitable process parameters for drum coaters of various sizes are described in an examplary manner in Examples 2, 9 and 13.

Preferably, the spray nozzle is attached to a spray arm which can be adjusted during the spraying process to ensure optimum spraying-on of the active ingredient.

The aqueous coating suspension comprises preferably about 20 to about 30%, particularly preferably 25-30%, of solids, based on the total weight of the coating suspension.

The end point of the spraying process can be determined in various ways. On the one hand, the amount of coating suspension to be sprayed on can be fixed; here, a typical spray loss of about 5 to 20%, preferably 10-15%, has to be taken into account. On the other hand, the end point can also be determined by in-process controls of the tablets to be coated. To this end, tablets are removed at defined intervals, preferably in the context of an at-line in-process control during the spraying process, and their layer thickness or the active ingredient content of the coating layer is determined by weighing and/or spectroscopic methods such as, for example, NIR, Raman or terahertz spectroscopy. Based on the in-process control values obtained, the spraying process is terminated at the exact point where the specified amount to be applied is reached. In principle, the spectroscopic methods mentioned are also suitable for an in-line process control. In this case, a spectroscopy probe is fitted into the drum coater such that during the spraying process individual tablets can be measured continuously without it being necessary to remove them from the drum coater.

A further coating without active ingredient, for example a photoprotective and/or colouring coating, can be applied to the mantle coating of the dosage form according to the invention if required. Excipients suitable for this purpose are, in principle, the same excipients as those used for the mantle coating. Materials suitable for this purpose are in particular polymers such as polyvinyl alcohol, hydroxypropylcellulose or hydroxypropylmethylcellulose, where appropriate in combination with suitable plasticizers such as, for example, polyethylene glycol and pigments such as, for example, titanium dioxide or iron oxides.

Preference is given in particular to the following commercially available preparations, "finished coatings" which already comprise further pharmaceutical excipients and which are simply dissolved in water, such as, for example, Opadry II 85F230009 Orange (Colorcon PVA-based finished coating), composition: partially hydrolyzed polyvinyl alcohol, talc, polyethylene glycol (PEG 3350), titanium dioxide, red iron oxide, yellow iron oxide and polysorbate 80 (Tween 80).

The present invention furthermore provides oral medicaments which are to be taken once every day and comprise a dosage form according to the invention.

The present invention furthermore provides the use of the dosage form according to the invention for the prophylaxis, secondary prophylaxis or treatment of cardiovascular disorders, for example high blood pressure.

The present invention furthermore provides the use of the dosage form according to the invention for preparing a medicament for the prophylaxis, secondary prophylaxis or treatment of cardiovascular disorders, for example high blood pressure, myocardial infarction, re-infarction, angina pectoris, coronary heart disease, chronic heart failure, transitory ischaemic attacks or insult.

The present invention furthermore provides a method for the prophylaxis, secondary prophylaxis or treatment of cardiovascular disorders by administering a dosage form according to the invention.

The combination of nifedipine or nisoldipine with an angiotension-II antagonist and a diuretic is particularly suitable for treating patients where monotherapy or dual combination therapy has not led to the desired lowering of blood pressure. The therapy-resistant patients are frequently those patients, where an adequate control of blood pressure in of particular importance. Both calcium antagonists and diuretics belong to the medicaments lowering blood pressure independently of the renin/angiotensin system; however, they differ in their mechanism of action. The calcium antagonists are primary vasodilators having a weak natriuretic action, whereas the opposite is true for the diuretics (thiazides). If the renin/angiotensin system is inhibited, the action of the diuretics is additive to that of the calcium antagonists. Surprisingly, we were able to show that the three-component combination described above led to an adequate control of blood pressure even in therapy-resistant patients.

Below, the invention is illustrated by preferred working examples; however, the invention is not limited to these examples. Unless indicated otherwise, all amounts given refer to percent by weight.

EXPERIMENTAL PART

Example 1: Osmotic Release System (Two-Chamber System)

Composition of the core in mg/core (declared content=30 mg of nifedipine)
Active Ingredient Layer:

| | |
|---|---:|
| nifedipine, micronized | 33.0 mg |
| hydroxypropylmethylcellulose (5 cp) | 8.2 mg |
| polyethylene oxide (molecular weight 200 000) | 122.2 mg |
| magnesium stearate | 0.4 mg |
| Sum: | 163.8 mg |

Osmosis Layer:

| | |
|---|---:|
| hydroxypropylmethylcellulose (5 cp) | 4.1 mg |
| sodium chloride | 23.9 mg |
| polyethylene oxide (molecular weight 5 000 000) | 52.9 mg |
| iron oxide red | 0.8 mg |
| magnesium stearate | 0.2 mg |
| Sum: | 81.9 mg |

Coat (Osmotic Membrane)

| | |
|---|---:|
| cellulose acetate | 32.3 mg |
| polyethylene glycol 3350 | 1.7 mg |
| Sum: | 34.0 mg |

Preparation:

The components of the active ingredient layer were mixed and subjected to dry granulation. The components of the osmosis layer, too, were mixed and subjected to dry granulation. On a bilayer tablet press, both sets of granules were compressed to give a bilayer tablet. The tablets were coated with a solution of cellulose acetate and polyethylene glycol in acetone and dried. Each tablet was then provided with an orifice of a diameter of 0.9 mm at the active ingredient side using a laser beam.

The cores obtained in this manner after the process had a diameter of 8.8 mm, a height of 4.6 mm and a weight of 276.6 mg±4.8 mg.

Example 1a: Osmotic Release System (Two-Chamber System)

Composition of the core in mg/core (declared content=60 mg of nifedipine)
Active Ingredient Layer:

| | |
|---|---:|
| nifedipine, micronized | 66.0 mg |
| hydroxypropylmethylcellulose (5 cp) | 16.4 mg |
| polyethylene oxide (molecular weight 200 000) | 244.4 mg |
| magnesium stearate | 0.8 mg |
| Sum: | 327.6 mg |

Osmosis Layer:

| | |
|---|---:|
| hydroxypropylmethylcellulose (5 cp) | 8.2 mg |
| sodium chloride | 47.8 mg |

-continued

| | |
|---|---|
| polyethylene oxide (molecular weight 5 000 000) | 105.8 mg |
| iron oxide red | 1.6 mg |
| magnesium stearate | 0.4 mg |
| Sum: | 163.8 mg |

Coat (Osmotic Membrane)

| | |
|---|---|
| cellulose acetate | 38.0 mg |
| polyethylene glycol 3350 | 2.0 mg |
| Sum: | 40.0 mg |

Preparation: Analogous to Example 1

The cores obtained in this manner after the process had a diameter of 10.6 mm, a height of 6.4 mm and a weight of 531.0 mg±3.9 mg.

Example 1b: Osmotic Release System (Two-Chamber System)

Composition of the core in mg/core (declared content=20 mg of nifedipine)

Active Ingredient Layer:

| | |
|---|---|
| nifedipine, micronized | 22.0 mg |
| hydroxypropylmethylcellulose (5 cp) | 5.5 mg |
| polyethylene oxide (molecular weight 200 000) | 81.5 mg |
| magnesium stearate | 0.3 mg |
| Sum: | 109.3 mg |

Osmosis Layer:

| | |
|---|---|
| hydroxypropylmethylcellulose (5 cp) | 3.6 mg |
| sodium chloride | 21.2 mg |
| polyethylene oxide (molecular weight 5 000 000) | 47.0 mg |
| iron oxide red | 0.7 mg |
| magnesium stearate | 0.2 mg |
| Sum: | 72.7 mg |

Coat (Osmotic Membrane)

| | |
|---|---|
| cellulose acetate | 33.2 mg |
| polyethylene glycol 3350 | 1.7 mg |
| Sum: | 34.9 mg |

Preparation: Analogous to Example 1

The cores obtained in this manner after the process had a diameter of 8.3 mm, a height of 4.2 mm and a weight of 216.0 mg±3.9 mg.

Example 2: Coated Cores

Preparation:

500 g of the finished coating mixture Colorcon Opadry II 85G25457, comprising a high proportion of red iron oxide particles, were reconstituted according to the instructions of the manufacturer by stirring the finished coating mixture into 2000 ml of purified water with the aid of a propeller stirrer, followed by stirring for another 45 minutes (coating suspension).

810.5 g (corresponds to 2930 items) of cores according to Example 1 (declared content=30 mg nifedipine) were introduced into a Coater Glatt GC300 and pre-warmed at an incoming air temperature of 60° C., an amount of incoming air of 120 m³/h and a drum speed of 10 rpm (revolutions per minute). The parameters incoming air temperature (60° C.), amount of incoming air (120 m³/h) and drum speed (10 rpm) were maintained for the entire coating process.

A round spray nozzle having a diameter of 0.8 mm at an atomizer pressure of 1.6 bar was chosen for spraying on the coating suspension, where, during the entire coating process, the mobile spray arm was in each case adjusted such that a homogeneous spray picture was obtained.

Using a spray rate that was gradually increased over the duration of the coating process, the coating suspension was applied to the cores, initially at 6 g/min and finally at 16 g/min, using the following stages:

| Time [min] | Spray rate [g/min] |
|---|---|
| 0-40 | 6 |
| 40-50 | 7 |
| 50-70 | 8 |
| 70-80 | 9 |
| 80-90 | 10 |
| 90-100 | 11 |
| 100-130 | 12 |
| 130-140 | 13 |
| 140-150 | 14 |
| 150-160 | 15 |
| 160-210 | 16 |

Total spraying time was 210 minutes. Without any further spraying, the tablets were then polished for a further 10 minutes in the drum.

Prior to the coating process, at various times during the coating process and immediately after the coating process, samples of the tablets were taken and the weight increase was determined.

The following results were obtained:

| Time [min] | Weight [mg] | Standard deviation [mg] |
|---|---|---|
| 0 | 276.6 | 4.8 |
| 30 | 298.5 | 4.8 |
| 60 | 311.0 | 5.3 |
| 90 | 326.3 | 6.8 |
| 120 | 351.6 | 9.1 |
| 150 | 380.4 | 8.4 |
| 180 | 414.4 | 10.9 |
| 210 | 446.1 | 12.2 |

Accordingly, the resulting tablets had a weight of 446.1 mg±12.2 mg. This corresponds to 170 mg of coating applied.

The tablets obtained had a diameter of 10.3 mm and a height of 6.0 mm. A cross-section of a tablet was examined under a direct-light microscope. The GITS core, consisting of the bilayer tablet having a cellulose acetate coating of a thickness of about 0.13 mm was coated with an even, uniformly red layer of a thickness of about 0.7 mm.

The tablets obtained were examined with an instrument for testing fracture resistance (Schleuniger Type 6D, Dr. Schleuniger Pharmatron AG, Solothurn, Switzerland). At the maximum possible force of 449 N, there was no breaking of the tablet, but only a slight plastic deformation of the film coating.

The tablets obtained were tested for abrasion in accordance with USP 31 (<1216> Tablet Friability). No abrasion was observed.

The tablets obtained were tested for decomposition time in accordance with USP 31 (<701> Disintegration) using purified water as medium at 37° C. and constantly monitored. After at most 25 minutes, the film coating was completely detached.

The tablets obtained were tested for release in accordance with USP 31 (<711> Dissolution) apparatus 2 (paddle apparatus) at 50 rpm (revolutions by minute) and 1000 ml of purified water as medium at 37° C. and constantly monitored. After at most 25 minutes, the film coating was completely detached.

Example 3: Osmotic Release System with Telmisartan-Comprising Mantle Layer

30% Telmisartan (based on the solids content of the coating suspension) are homogeneously suspended in a coating suspension based on a polyvinyl alcohol derivative.

A number of cores according to Example 1, 1a or 1b are introduced into a drum coater, such that the coater is charged with about 75% of the typical batch size. According to Example 2, the telmisartan-comprising coating suspension is applied onto these cores until the total weight of the tablets corresponds to about 125% of a typical batch size of the coater.

Example 4: Osmotic Release System with Candesartan-Comprising Mantle Layer

20% Candesartan cilexetil (based on the solids content of the coating suspension) are homogeneously suspended in a coating suspension based on a polyvinyl alcohol derivative.

A number of cores according to Example 1, 1a or 1b are introduced into a drum coater, such that the coater is charged with about 80% of the typical batch size. According to Example 2, the candesartan cilexetil-comprising coating suspension is applied onto these cores until the total weight of the tablets corresponds to about 120% of a typical batch size of the coater.

Example 5: Examplary Compositions of Tablets Comprising Nifedipine+Telmisartan All data in mg, preparation according to Example 1, 1a, 1b, 2 and 3, with amounts and concentrations adapted.

| Formulation | 5a | 5b | 5c | 5d | 5e | 5f | 5g | 5h | 5i | 5j | 5k | 5l |
|---|---|---|---|---|---|---|---|---|---|---|---|---|
| Active ingredient layer: | | | | | | | | | | | | |
| nifedipine, micronized | 33.0 | 33.0 | 33.0 | 33.0 | 33.0 | 33.0 | 33.0 | 33.0 | 22.0 | 22.0 | 66.0 | 66.0 |
| HMPC (5 cp) | 8.2 | 8.2 | 8.2 | 8.2 | 8.2 | 8.2 | 8.2 | 8.2 | 5.5 | 5.5 | 16.4 | 16.4 |
| PEO 200 000 | 122.2 | 122.2 | 122.2 | 122.2 | 122.2 | 122.2 | 122.2 | 122.2 | 81.5 | 81.5 | 244.4 | 244.4 |
| magnesium stearate | 0.4 | 0.4 | 0.4 | 0.4 | 0.4 | 0.4 | 0.4 | 0.4 | 0.3 | 0.3 | 0.8 | 0.8 |
| Osmosis layer: | | | | | | | | | | | | |
| HMPC (5 cp) | 4.1 | 4.1 | 4.1 | 4.1 | 4.1 | 4.1 | 4.1 | 4.1 | 3.6 | 3.6 | 8.2 | 8.2 |
| sodium chloride | 23.9 | 23.9 | 23.9 | 23.9 | 23.9 | 23.9 | 23.9 | 23.9 | 21.2 | 21.2 | 47.8 | 47.8 |
| PEO 5 000 000 | 52.9 | 52.9 | 52.9 | 52.9 | 52.9 | 52.9 | 52.9 | 52.9 | 47.0 | 47.0 | 105.8 | 105.8 |
| iron oxide red | 0.8 | 0.8 | 0.8 | 0.8 | 0.8 | 0.8 | 0.8 | 0.8 | 0.7 | 0.7 | 1.6 | 1.6 |
| magnesium stearate | 0.2 | 0.2 | 0.2 | 0.2 | 0.2 | 0.2 | 0.2 | 0.2 | 0.2 | 0.2 | 0.4 | 0.4 |
| Osmotic membrane | | | | | | | | | | | | |
| cellulose acetate | 32.3 | 32.3 | 32.3 | 32.3 | 32.3 | 32.3 | 32.3 | 32.3 | 33.2 | 33.2 | 38.0 | 38.0 |
| PEG 3350 | 1.7 | 1.7 | 1.7 | 1.7 | 1.7 | 1.7 | 1.7 | 1.7 | 1.7 | 1.7 | 2.0 | 2.0 |
| Active ingredient coating | | | | | | | | | | | | |
| telmisartan, micronized | 20.0 | 20.0 | 20.0 | 20.0 | 80.0 | 80.0 | 80.0 | 80.0 | 20.0 | 80.0 | 20.0 | 80.0 |
| iron oxide red | 1.0 | 1.0 | 1.0 | 1.0 | 1.0 | 1.0 | 1.0 | 1.0 | 1.0 | 1.0 | 1.0 | 1.0 |
| Kollicoat IR | 53.5 | 51.4 | | | 116.0 | 99.1 | | | | | | |
| Kollidon VA 64 | 7.5 | 5.7 | | | 16.0 | 11.0 | | | | | | |
| titanium dioxide | | 11.8 | | | | 22.7 | | | | | | |
| kaolin | 12.0 | 13.4 | | | 26.0 | 25.9 | | | | | | |
| sodium lauryl sulphate | 2.0 | 1.7 | | | 4.0 | 3.3 | | | | | | |
| Sepifilm IR colourless | | | 84.0 | | | | 162.0 | | | | | |
| Opadry II 85F28393 | | | | 84.0 | | | | 162.0 | 84.0 | 121.5 | 84.0 | 189.0 |

Example 6: Examplary Compositions of Tablets Comprising Nifedipine+Candesartan Cilexetil All data in mg, preparation according to Example 1, 1a, 1b, 2 and 4, with amount and concentrations adapted

| Formulation | 6a | 6b | 6c | 6d | 6e | 6f | 6g | 6h | 6i | 6j | 6k | 6l |
|---|---|---|---|---|---|---|---|---|---|---|---|---|
| Active ingredient layer: | | | | | | | | | | | | |
| nifedipine, micronized | 33.0 | 33.0 | 33.0 | 33.0 | 33.0 | 33.0 | 33.0 | 33.0 | 22.0 | 22.0 | 66.0 | 66.0 |
| HMPC (5 cp) | 8.2 | 8.2 | 8.2 | 8.2 | 8.2 | 8.2 | 8.2 | 8.2 | 5.5 | 5.5 | 16.4 | 16.4 |
| PEO 200 000 | 122.2 | 122.2 | 122.2 | 122.2 | 122.2 | 122.2 | 122.2 | 122.2 | 81.5 | 81.5 | 244.4 | 244.4 |
| magnesium stearate | 0.4 | 0.4 | 0.4 | 0.4 | 0.4 | 0.4 | 0.4 | 0.4 | 0.3 | 0.3 | 0.8 | 0.8 |
| Osmosis layer: | | | | | | | | | | | | |
| HMPC (5 cp) | 4.1 | 4.1 | 4.1 | 4.1 | 4.1 | 4.1 | 4.1 | 4.1 | 3.6 | 3.6 | 8.2 | 8.2 |
| sodium chloride | 23.9 | 23.9 | 23.9 | 23.9 | 23.9 | 23.9 | 23.9 | 23.9 | 21.2 | 21.2 | 47.8 | 47.8 |
| PEO 5 000 000 | 52.9 | 52.9 | 52.9 | 52.9 | 52.9 | 52.9 | 52.9 | 52.9 | 47.0 | 47.0 | 105.8 | 105.8 |
| iron oxide red | 0.8 | 0.8 | 0.8 | 0.8 | 0.8 | 0.8 | 0.8 | 0.8 | 0.7 | 0.7 | 1.6 | 1.6 |
| magnesium stearate | 0.2 | 0.2 | 0.2 | 0.2 | 0.2 | 0.2 | 0.2 | 0.2 | 0.2 | 0.2 | 0.4 | 0.4 |
| Osmotic membrane | | | | | | | | | | | | |
| cellulose acetate | 32.3 | 32.3 | 32.3 | 32.3 | 32.3 | 32.3 | 32.3 | 32.3 | 33.2 | 33.2 | 38.0 | 38.0 |
| PEG 3350 | 1.7 | 1.7 | 1.7 | 1.7 | 1.7 | 1.7 | 1.7 | 1.7 | 1.7 | 1.7 | 2.0 | 2.0 |
| Active ingredient coating | | | | | | | | | | | | |
| candesartan cilexetil, micronized | 4.0 | 4.0 | 4.0 | 4.0 | 32.0 | 32.0 | 32.0 | 32.0 | 4.0 | 32.0 | 4.0 | 32.0 |
| iron oxide red | 1.0 | 1.0 | 1.0 | 1.0 | 1.0 | 1.0 | 1.0 | 1.0 | 1.0 | 1.0 | 1.0 | 1.0 |
| Kollicoat IR | 10.7 | 12.2 | | | 85.6 | 80.8 | | | | | | |
| Kollidon VA 64 | 1.5 | 1.4 | | | 12.0 | 9.0 | | | | | | |
| titanium dioxide | | 2.8 | | | | 18.5 | | | | | | |
| kaolin | 2.4 | 3.2 | | | 19.2 | 21.1 | | | | | | |
| sodium lauryl sulphate | 0.4 | 0.4 | | | 3.2 | 2.6 | | | | | | |
| Sepifilm IR colourless | | | 20.0 | | | | 132.0 | | | | | |
| Opadry II 85F28393 | | | | 20.0 | | | | 132.0 | 20.0 | 99.0 | 20.0 | 132.0 |

Example 7: Examplary Compositions of Tablets Comprising Nifedipine+Telmisartan+HCT All data in mg, preparation according to Example 1, 1a, 1b, 2 and 3, with amount and concentrations adapted

| Formulation | 7a | 7b | 7c | 7d | 7e | 7f | 7g | 7h | 7i | 7j | 7k | 7l |
|---|---|---|---|---|---|---|---|---|---|---|---|---|
| Active ingredient layer: | | | | | | | | | | | | |
| nifedipine, micronized | 33.0 | 33.0 | 33.0 | 33.0 | 33.0 | 33.0 | 33.0 | 33.0 | 22.0 | 22.0 | 66.0 | 66.0 |
| HMPC (5 cp) | 8.2 | 8.2 | 8.2 | 8.2 | 8.2 | 8.2 | 8.2 | 8.2 | 5.5 | 5.5 | 16.4 | 16.4 |
| PEO 200 000 | 122.2 | 122.2 | 122.2 | 122.2 | 122.2 | 122.2 | 122.2 | 122.2 | 81.5 | 81.5 | 244.4 | 244.4 |
| magnesium stearate | 0.4 | 0.4 | 0.4 | 0.4 | 0.4 | 0.4 | 0.4 | 0.4 | 0.3 | 0.3 | 0.8 | 0.8 |
| Osmosis layer: | | | | | | | | | | | | |
| HMPC (5 cp) | 4.1 | 4.1 | 4.1 | 4.1 | 4.1 | 4.1 | 4.1 | 4.1 | 3.6 | 3.6 | 8.2 | 8.2 |
| sodium chloride | 23.9 | 23.9 | 23.9 | 23.9 | 23.9 | 23.9 | 23.9 | 23.9 | 21.2 | 21.2 | 47.8 | 47.8 |
| PEO 5 000 000 | 52.9 | 52.9 | 52.9 | 52.9 | 52.9 | 52.9 | 52.9 | 52.9 | 47.0 | 47.0 | 105.8 | 105.8 |
| iron oxide red | 0.8 | 0.8 | 0.8 | 0.8 | 0.8 | 0.8 | 0.8 | 0.8 | 0.7 | 0.7 | 1.6 | 1.6 |
| magnesium stearate | 0.2 | 0.2 | 0.2 | 0.2 | 0.2 | 0.2 | 0.2 | 0.2 | 0.2 | 0.2 | 0.4 | 0.4 |
| Osmotic membrane | | | | | | | | | | | | |
| cellulose acetate | 32.3 | 32.3 | 32.3 | 32.3 | 32.3 | 32.3 | 32.3 | 32.3 | 33.2 | 33.2 | 38.0 | 38.0 |
| PEG 3350 | 1.7 | 1.7 | 1.7 | 1.7 | 1.7 | 1.7 | 1.7 | 1.7 | 1.7 | 1.7 | 2.0 | 2.0 |

-continued

| Formulation | 7a | 7b | 7c | 7d | 7e | 7f | 7g | 7h | 7i | 7j | 7k | 7l |
|---|---|---|---|---|---|---|---|---|---|---|---|---|
| Active ingredient coating | | | | | | | | | | | | |
| telmisartan, micronized | 40.0 | 40.0 | 40.0 | 40.0 | 80.0 | 80.0 | 80.0 | 80.0 | 40.0 | 80.0 | 40.0 | 80.0 |
| hydrochloro-thiazide, micronized | 12.5 | 12.5 | 12.5 | 12.5 | 25.0 | 25.0 | 25.0 | 25.0 | 12.5 | 12.5 | 12.5 | 25.0 |
| iron oxide red | 1.0 | 1.0 | 1.0 | 1.0 | 1.0 | 1.0 | 1.0 | 1.0 | 1.0 | 1.0 | 1.0 | 1.0 |
| Kollicoat IR | 116.0 | 99.1 | | | 16.0 | 99.1 | | | | | | |
| Kollidon VA 64 | 16.0 | 11.0 | | | 16.0 | 11.0 | | | | | | |
| titanium dioxide | | 22.7 | | | | 22.7 | | | | | | |
| kaolin | 26.0 | 25.9 | | | 26.0 | 25.9 | | | | | | |
| sodium lauryl sulphate | 4.0 | 3.3 | | | 4.0 | 3.3 | | | | | | |
| Sepifilm IR colourless | | | 162.0 | | | | 162.0 | | | | | |
| Opadry II 85F28393 | | | | 62.0 | | | | 62.0 | 121.5 | 121.5 | 89.0 | 189.0 |

Example 8: Examplary Compositions of Tablets Comprising Nifedipine+Candesartan Cilexetil+HCT All data in mg, preparation according to Example 1, 1a, 1b, 2 and 4, with amount and concentrations adapted

| Formulation | 8a | 8b | 8c | 8d | 8e | 8f | 8g | 8h | 8i | 8j | 8k | 8l |
|---|---|---|---|---|---|---|---|---|---|---|---|---|
| Active ingredient layer: | | | | | | | | | | | | |
| nifedipine, micronized | 33.0 | 33.0 | 33.0 | 33.0 | 33.0 | 33.0 | 33.0 | 33.0 | 22.0 | 22.0 | 66.0 | 66.0 |
| HMPC (5 cp) | 8.2 | 8.2 | 8.2 | 8.2 | 8.2 | 8.2 | 8.2 | 8.2 | 5.5 | 5.5 | 16.4 | 16.4 |
| PEO 200 000 | 122.2 | 122.2 | 122.2 | 122.2 | 122.2 | 122.2 | 122.2 | 122.2 | 81.5 | 81.5 | 244.4 | 244.4 |
| magnesium stearate | 0.4 | 0.4 | 0.4 | 0.4 | 0.4 | 0.4 | 0.4 | 0.4 | 0.3 | 0.3 | 0.8 | 0.8 |
| Osmosis layer: | | | | | | | | | | | | |
| HMPC (5 cp) | 4.1 | 4.1 | 4.1 | 4.1 | 4.1 | 4.1 | 4.1 | 4.1 | 3.6 | 3.6 | 8.2 | 8.2 |
| sodium chloride | 23.9 | 23.9 | 23.9 | 23.9 | 23.9 | 23.9 | 23.9 | 23.9 | 21.2 | 21.2 | 47.8 | 47.8 |
| PEO 5 000 000 | 52.9 | 52.9 | 52.9 | 52.9 | 52.9 | 52.9 | 52.9 | 52.9 | 47.0 | 47.0 | 105.8 | 105.8 |
| iron oxide red | 0.8 | 0.8 | 0.8 | 0.8 | 0.8 | 0.8 | 0.8 | 0.8 | 0.7 | 0.7 | 1.6 | 1.6 |
| magnesium stearate | 0.2 | 0.2 | 0.2 | 0.2 | 0.2 | 0.2 | 0.2 | 0.2 | 0.2 | 0.2 | 0.4 | 0.4 |
| Osmotic membrane | | | | | | | | | | | | |
| cellulose acetate | 32.3 | 32.3 | 32.3 | 32.3 | 32.3 | 32.3 | 32.3 | 32.3 | 33.2 | 33.2 | 38.0 | 38.0 |
| PEG 3350 | 1.7 | 1.7 | 1.7 | 1.7 | 1.7 | 1.7 | 1.7 | 1.7 | 1.7 | 1.7 | 2.0 | 2.0 |
| Active ingredient coating | | | | | | | | | | | | |
| candesartan cilexetil, micronized | 8.0 | 8.0 | 8.0 | 8.0 | 16.0 | 16.0 | 16.0 | 16.0 | 8.0 | 16.0 | 8.0 | 16.0 |
| hydrochloro-thiazide, micronized | 12.5 | 12.5 | 12.5 | 12.5 | 12.5 | 12.5 | 12.5 | 12.5 | 12.5 | 12.5 | 12.5 | 12.5 |
| iron oxide red | 1.0 | 1.0 | 1.0 | 1.0 | 1.0 | 1.0 | 1.0 | 1.0 | 1.0 | 1.0 | 1.0 | 1.0 |
| Kollicoat IR | 85.6 | 80.8 | | | 85.6 | 80.8 | | | | | | |
| Kollidon VA 64 | 12.0 | 9.0 | | | 12.0 | 9.0 | | | | | | |
| titanium dioxide | | 18.5 | | | | 18.5 | | | | | | |
| kaolin | 19.2 | 21.1 | | | 19.2 | 21.1 | | | | | | |
| sodium lauryl sulphate | 3.2 | 2.6 | | | 3.2 | 2.6 | | | | | | |
| Sepifilm IR colourless | | | 132.0 | | | | 132.0 | | | | | |
| Opadry II 85F28393 | | | | 132.0 | | | | 132.0 | 99.0 | 99.0 | 132.0 | 132.0 |

Example 9: Preparation of Osmotic Release Systems Comprising 60 mg of Nifedipine with a Mantle Layer Comprising 32 mg of Candesartan Cilexetil and a Colouring Coating To prepare the coating suspension, 240 g of micronized candesartan cilexetil (having a particle size distribution described by $X_{50}<3$ μm and $X_{90}<7$ μm) are suspended in 1440 g of purified water using a propeller stirrer. After addition of 360 g of the finished coating Opadry II 85F19250 Clear and further stirring for about 45 minutes, a homogeneous suspension was obtained.

3 kg of cores according to Example 1a were introduced into a drum coater BFC 5 from L. B. BOHLE Maschinen+Verfahren GmbH, D-59320 Ennigerloh, fitted with the undivided small drum and a spray arm having 2 spray nozzles and pre-warmed at an incoming air temperature of 60° C., an amount of incoming air of 160 m³/h and a drum speed of 18 rpm (revolutions per minute). The parameters incoming air temperature (60° C.), amount of incoming air (160 m³/h) and drum speed (18 rpm) were maintained for the entire coating process.

For spraying-on the coating suspension, use was made of two nozzles having a diameter of 1.0 mm, where elipsoidal spray cones were obtained using a spray pressure of 0.8 bar and a formation pressure of 0.7 bar. During the entire coating process, the spray arm was adjusted such that a homogeneous spray picture was obtained.

Using a spray rate that was gradually increased over the duration of the coating process, the coating suspension was applied to the cores, during the first hour at 8 g/min and from the second hour onwards at 12 g/min.

Total spraying time was about 150 minutes. Without any further spraying, the tablets were then polished for a further 30 minutes in the drum at a drum speed of 12 rpm.

Prior to the coating process, at various times during the coating process and immediately after the coating process, samples of the tablets were taken and the weight increase was determined. The end point of the spraying process was determined by the weight increase.

The following results were obtained:

| Time [min] | Weight [mg] | Standard deviation [mg] |
| --- | --- | --- |
| 0 | 531.0 | 3.9 |
| 30 | 544.8 | 4.1 |
| 60 | 558.3 | 4.6 |
| 90 | 572.9 | 3.4 |
| 120 | 593.2 | 6.4 |
| 150 | 612.6 | 6.5 |

Accordingly, the resulting tablets had a weight of 612.6 mg±6.5 mg. This corresponds to a theoretical applied coating of about 81.6 mg. The tablets obtained had a diameter of 10.9 mm and a height of 7.0 mm. The tablets obtained had a smooth, slightly glossy surface.

The fracture resistance of the tablets obtained was examined with an instrument for testing fracture resistance (Schleuniger Type 6D, Dr. Schleuniger Pharmatron AG, Solothurn, Switzerland). Only forces of more than 400 N caused the tablets to break.

The tablets obtained were tested for abrasion in accordance with USP 31 (<1216> Tablet Friability). No abrasion was observed.

The tablets obtained were tested for decomposition time in accordance with USP 31 (<701> Disintegration) using purified water as medium at 37° C. and constantly monitored. After at most 10 minutes, the film coating was completely detached.

The tablets obtained were tested for release in accordance with USP 31 (<711> Dissolution) apparatus 2 (paddle apparatus) at 75 rpm (revolutions by minute) and 900 ml of acetate buffer pH 4.5 with addition of 0.6% of sodium lauryl sulphate as medium at 37° C. The active ingredient content in the release medium was determined by HPLC using UV detection. After 30 minutes, at least 80% of the candesartan cilexetil had been released (lowest value of 12 individual values). The nifedipine release was 10% (mean of 6 individual values, range of the individual values: 7-12%) after 4 hours, 52% (45-56%) after 12 hours and 98% (91-100%) after 24 hours.

The tablets obtained were tested for release in accordance with USP 31 (<711> Dissolution) apparatus 2 (paddle apparatus) at 75 rpm (revolutions by minute) and 900 ml of 0.1 N hydrochloric acid (pH 1.0) with addition of 0.6% of sodium lauryl sulphate as medium at 37° C. The active ingredient content in the release medium was determined by HPLC using UV detection. After 30 minutes, at least 88% of the candesartan cilexetil had been released (lowest value of 6 individual values).

Of 10 tablets randomly selected from the tablets obtained, the individual content of candesartan cilexetil was in each case determined by HPLC using UV detection. The mean of the individual content was 32.0 mg at a standard deviation of 5.0%, based on the mean. In the test for content uniformity, this resulted in an acceptance value of 12.1%.

For application of an additional colouring coating, 3.065 kg of the tablets were introduced into a drum coater BFC 5 from L. B. BOHLE Maschinen+Verfahren GmbH, D-59320 Ennigerloh and pre-warmed at an incoming air temperature of 60° C., an amount of incoming air of 160 m³/h and a drum speed of 18 rpm (revolutions per minute). The parameters incoming air temperature (60° C.), amount of incoming air (160 m³/h) and drum speed (18 rpm) were maintained for the entire coating process. For spraying-on the coating suspension, use was made of two nozzles having a diameter of 1.0 mm, where elipsoidal spray cones were obtained using a spray pressure of 0.8 bar and a formation pressure of 0.7 bar. During the entire coating process, the spray arm was adjusted such that a homogeneous spray picture was obtained.

The coating suspension was prepared by dispersing 165 g of the finished coating Opadry II 85F230009 in 495 g of purified water. 444 g of the resulting colouring coating suspension were applied onto the tablets at a spray rate of 8 g/min Total spraying time was about 55 minutes. The end point of the spraying process was determined by the specified amount of coating suspension to be sprayed on. Without any further spraying, the tablets were then polished for a further 15 minutes in the drum.

The resulting coated tablets had a weight of 635.7 mg±6.7 mg. This corresponds to a theoretical applied coating of about 23.1 mg. The coated tablets obtained had a diameter of 11.0 mm and a height of 7.1 mm. The coated tablets obtained had a smooth, slightly glossy surface.

The release of active ingredient from the coated tablets is delayed by less than 5 minutes compared to the release from the tablets without colouring coating.

Example 10: Compositions of Tablets Comprising Nifedipine+Candesartan Cilexetil All data in mg, preparation according to Example 1, 1a, 1b and 9, with amounts and concentrations adapted

| Formulation | 10a | 10b | 10c | 10d | 10e | 10f | 10g | 10h | 10i | 10j | 10k | 10l |
|---|---|---|---|---|---|---|---|---|---|---|---|---|
| Active ingredient layer: | | | | | | | | | | | | |
| nifedipine, micronized | 66.0 | 66.0 | 66.0 | 66.0 | 33.0 | 33.0 | 33.0 | 33.0 | 22.0 | 22.0 | 22.0 | 22.0 |
| HMPC (5 cp) | 16.4 | 16.4 | 16.4 | 16.4 | 8.2 | 8.2 | 8.2 | 8.2 | 5.5 | 5.5 | 5.5 | 5.5 |
| PEO 200 000 | 244.4 | 244.4 | 244.4 | 244.4 | 122.2 | 122.2 | 122.2 | 122.2 | 81.5 | 81.5 | 81.5 | 81.5 |
| magnesium stearate | 0.8 | 0.8 | 0.8 | 0.8 | 0.4 | 0.4 | 0.4 | 0.4 | 0.3 | 0.3 | 0.3 | 0.3 |
| Osmosis layer: | | | | | | | | | | | | |
| HMPC (5 cp) | 8.2 | 8.2 | 8.2 | 8.2 | 4.1 | 4.1 | 4.1 | 4.1 | 3.6 | 3.6 | 3.6 | 3.6 |
| sodium chloride | 47.8 | 47.8 | 47.8 | 47.8 | 23.9 | 23.9 | 23.9 | 23.9 | 21.2 | 21.2 | 21.2 | 21.2 |
| PEO 5 000 000 | 105.8 | 105.8 | 105.8 | 105.8 | 52.9 | 52.9 | 52.9 | 52.9 | 47.0 | 47.0 | 47.0 | 47.0 |
| iron oxide red | 1.6 | 1.6 | 1.6 | 1.6 | 0.8 | 0.8 | 0.8 | 0.8 | 0.7 | 0.7 | 0.7 | 0.7 |
| magnesium stearate | 0.4 | 0.4 | 0.4 | 0.4 | 0.2 | 0.2 | 0.2 | 0.2 | 0.2 | 0.2 | 0.2 | 0.2 |
| Osmotic membrane | | | | | | | | | | | | |
| cellulose acetate | 38.0 | 38.0 | 38.0 | 38.0 | 32.3 | 32.3 | 32.3 | 32.3 | 33.2 | 33.2 | 33.2 | 33.2 |
| PEG 3350 | 2.0 | 2.0 | 2.0 | 2.0 | 1.7 | 1.7 | 1.7 | 1.7 | 1.7 | 1.7 | 1.7 | 1.7 |
| Active ingredient coating | | | | | | | | | | | | |
| candesartan cilexetil, micronized | 32.0 | 16.0 | 8.0 | 4.0 | 32.0 | 16.0 | 8.0 | 4.0 | 32.0 | 16.0 | 8.0 | 4.0 |
| Opadry II 85F19250 | 48.0 | 24.0 | 12.0 | 16.0* | 48.0 | 24.0 | 12.0 | 16.0* | 48.0 | 24.0 | 12.0 | 16.0* |
| Colouring coating | | | | | | | | | | | | |
| Opadry II 85F230009 | 20.0 | 20.0 | 20.0 | 20.0 | 16.0 | 16.0 | 16.0 | 16.0 | 14.0 | 14.0 | 14.0 | 14.0 |

*with an otherwise identical composition, the amount of finished coating may be varied between 6.0 and 16.0 mg.

Example 11: Examplary Compositions of Tablets Comprising Nifedipine+Candesartan Cilexetil+a Diuretic, Selected from the Group Consisting of Chlorthalidone and Hydrochlorothiazide, where the Active Ingredients are Present Together in a Mantle Coating All data in mg, preparation according to Example 1, 1a, 1b and 9, with amounts and concentrations adapted.

| Formulation | 11a | 11b | 11c | 11d | 11e | 11f | 11g | 11h | 11i | 11j | 11k | 11l |
|---|---|---|---|---|---|---|---|---|---|---|---|---|
| Active ingredient layer: | | | | | | | | | | | | |
| nifedipine, micronized | 33.0 | 33.0 | 33.0 | 33.0 | 33.0 | 33.0 | 33.0 | 33.0 | 22.0 | 22.0 | 66.0 | 66.0 |
| HMPC (5 cp) | 8.2 | 8.2 | 8.2 | 8.2 | 8.2 | 8.2 | 8.2 | 8.2 | 5.5 | 5.5 | 16.4 | 16.4 |
| PEO 200 000 | 122.2 | 122.2 | 122.2 | 122.2 | 122.2 | 122.2 | 122.2 | 122.2 | 81.5 | 81.5 | 244.4 | 244.4 |
| magnesium stearate | 0.4 | 0.4 | 0.4 | 0.4 | 0.4 | 0.4 | 0.4 | 0.4 | 0.3 | 0.3 | 0.8 | 0.8 |
| Osmosis layer: | | | | | | | | | | | | |
| HMPC (5 cp) | 4.1 | 4.1 | 4.1 | 4.1 | 4.1 | 4.1 | 4.1 | 4.1 | 3.6 | 3.6 | 8.2 | 8.2 |
| sodium chloride | 23.9 | 23.9 | 23.9 | 23.9 | 23.9 | 23.9 | 23.9 | 23.9 | 21.2 | 21.2 | 47.8 | 47.8 |
| PEO 5 000 000 | 52.9 | 52.9 | 52.9 | 52.9 | 52.9 | 52.9 | 52.9 | 52.9 | 47.0 | 47.0 | 105.8 | 105.8 |
| iron oxide red | 0.8 | 0.8 | 0.8 | 0.8 | 0.8 | 0.8 | 0.8 | 0.8 | 0.7 | 0.7 | 1.6 | 1.6 |
| magnesium stearate | 0.2 | 0.2 | 0.2 | 0.2 | 0.2 | 0.2 | 0.2 | 0.2 | 0.2 | 0.2 | 0.4 | 0.4 |
| Osmotic membrane | | | | | | | | | | | | |
| cellulose acetate | 4.1 | 4.1 | 4.1 | 4.1 | 4.1 | 4.1 | 4.1 | 4.1 | 33.2 | 33.2 | 38.0 | 38.0 |
| PEG 3350 | 23.9 | 23.9 | 23.9 | 23.9 | 23.9 | 23.9 | 23.9 | 23.9 | 1.7 | 1.7 | 2.0 | 2.0 |
| Active ingredient coating | | | | | | | | | | | | |
| candesartan cilexetil, micronized | 8.0 | 8.0 | 16.0 | 32.0 | 8.0 | 8.0 | 16.0 | 32.0 | 4.0 | 4.0 | 32.0 | 32.0 |
| hydrochloro-thiazide, micronized | 12.5 | 25.0 | 25.0 | 25.0 | | | | | 12.5 | | 25.0 | |

-continued

| Formulation | 11a | 11b | 11c | 11d | 11e | 11f | 11g | 11h | 11i | 11j | 11k | 11l |
|---|---|---|---|---|---|---|---|---|---|---|---|---|
| chlorthalidone, micronized | | | | | 12.5 | 25.0 | 25.0 | 50.0 | | 12.5 | | 50.0 |
| Opadry II 85F19250 | 30.75 | 49.5 | 61.5 | 85.5 | 30.75 | 49.5 | 61.5 | 123.0 | 24.75 | 24.75 | 85.5 | 123.0 |
| Colouring coating | | | | | | | | | | | | |
| Opadry II 85F230009 | 16.0 | 16.0 | 16.0 | 16.0 | 16.0 | 16.0 | 16.0 | 16.0 | 14.0 | 14.0 | 20.0 | 20.0 |

Example 12: Examplary Compositions of Tablets Comprising Nifedipine+Candesartan Cilexetil+a Diuretic, Selected from the Group Consisting of Chlorthalidone and Hydrochlorothiazide, where the Active Ingredients are Present Together in a Mantle Coating in Separate Layers Applied in Succession All data in mg, preparation according to Example 1, 1a, 1b and 9, with amounts and concentrations adapted purified water using a propeller stirrer. After addition of 396 g of the finished coating Opadry II 85F19250 Clear and further stirring for about 45 minutes, a homogeneous suspension was obtained.

700 g (corresponds to 3240 items) of cores according to Example 1c (declared content=20 mg nifedipine) were introduced into a Coater Glatt GC300 and pre-warmed at an incoming air temperature of 60° C., an amount of incoming air of 120 m³/h and a drum speed of 16 rpm (rotations per

| Formulation | 12a | 12b | 12c | 12d | 12e | 12f | 12g | 12h | 12i | 12j | 12k | 12l |
|---|---|---|---|---|---|---|---|---|---|---|---|---|
| Active ingredient layer: | | | | | | | | | | | | |
| nifedipine, micronized | 33.0 | 33.0 | 33.0 | 33.0 | 33.0 | 33.0 | 33.0 | 33.0 | 22.0 | 22.0 | 66.0 | 66.0 |
| HMPC (5 cp) | 8.2 | 8.2 | 8.2 | 8.2 | 8.2 | 8.2 | 8.2 | 8.2 | 5.5 | 5.5 | 16.4 | 16.4 |
| PEO 200 000 | 122.2 | 122.2 | 122.2 | 122.2 | 122.2 | 122.2 | 122.2 | 122.2 | 81.5 | 81.5 | 244.4 | 244.4 |
| magnesium stearate | 0.4 | 0.4 | 0.4 | 0.4 | 0.4 | 0.4 | 0.4 | 0.4 | 0.3 | 0.3 | 0.8 | 0.8 |
| Osmosis layer: | | | | | | | | | | | | |
| HMPC (5 cp) | 4.1 | 4.1 | 4.1 | 4.1 | 4.1 | 4.1 | 4.1 | 4.1 | 3.6 | 3.6 | 8.2 | 8.2 |
| sodium chloride | 23.9 | 23.9 | 23.9 | 23.9 | 23.9 | 23.9 | 23.9 | 23.9 | 21.2 | 21.2 | 47.8 | 47.8 |
| PEO 5 000 000 | 52.9 | 52.9 | 52.9 | 52.9 | 52.9 | 52.9 | 52.9 | 52.9 | 47.0 | 47.0 | 105.8 | 105.8 |
| iron oxide red | 0.8 | 0.8 | 0.8 | 0.8 | 0.8 | 0.8 | 0.8 | 0.8 | 0.7 | 0.7 | 1.6 | 1.6 |
| magnesium stearate | 0.2 | 0.2 | 0.2 | 0.2 | 0.2 | 0.2 | 0.2 | 0.2 | 0.2 | 0.2 | 0.4 | 0.4 |
| Osmotic membrane | | | | | | | | | | | | |
| cellulose acetate | 4.1 | 4.1 | 4.1 | 4.1 | 4.1 | 4.1 | 4.1 | 4.1 | 33.2 | 33.2 | 38.0 | 38.0 |
| PEG 3350 | 23.9 | 23.9 | 23.9 | 23.9 | 23.9 | 23.9 | 23.9 | 23.9 | 1.7 | 1.7 | 2.0 | 2.0 |
| Active ingredient coating 1* | | | | | | | | | | | | |
| candesartan cilexetil, micronized | | 8.0 | 16.0 | 16.0 | | 8.0 | 16.0 | 16.0 | 4.0 | 4.0 | 32.0 | 32.0 |
| Opadry II 85F19250 | | 12.0 | 24.0 | 24.0 | | 12.0 | 24.0 | 24.0 | 16.0 | 16.0 | 48.0 | 48.0 |
| Active ingredient coating 2* | | | | | | | | | | | | |
| hydrochloro-thiazide, micronized | 12.5 | 12.5 | 12.5 | 25.0 | | | | | 12.5 | | 25.0 | |
| chlorthalidone, micronized | | | | | 12.5 | 12.5 | 12.5 | 25.0 | | 12.5 | | 50.0 |
| Opadry II 85F19250 | 18.75 | 18.75 | 18.75 | 37.5 | 18.75 | 18.75 | 18.75 | 37.5 | 18.75 | 18.75 | 37.5 | 75.0 |
| Colouring coating | | | | | | | | | | | | |
| Opadry II 85F230009 | 16.0 | 16.0 | 16.0 | 16.0 | 16.0 | 16.0 | 16.0 | 16.0 | 14.0 | 14.0 | 20.0 | 20.0 |

*The order in which the two active ingredient-comprising coating layers are applied can be reversed.

Example 13: Preparation of Osmotic Release System Comprising 20 mg of Nifedipine Having a Mantle Layer Comprising 70 mg of Telmisartan To prepare the coating suspension, 264 g of micronized telmisartan (having a particle size distribution described by $X_{50} < 2$ μm and $X_{90} < 5$ μm) are suspended in 1584 g of minute). The parameters incoming air temperature (60° C.), amount of incoming air (120 m³/h) and drum speed (16 rpm) were maintained for the entire coating process.

A round spray nozzle having a diameter of 0.8 mm at an atomizer pressure of 1.6 bar was chosen for spraying on the coating suspension, where, during the entire coating process, the mobile spray arm was in each case adjusted such that a homogeneous spray picture was obtained.

Using a spray rate that was gradually increased over the duration of the coating process, the coating suspension was applied to the cores, during the first hour at 3.5 g/min and from the second hour onwards at 7 g/min.

Total spraying time was 300 minutes. Without any further spraying, the tablets were then polished for a further 10 minutes in the drum.

Prior to the coating process, at various times during the coating process and immediately after the coating process, samples of the tablets were taken and the weight increase was determined. The end point of the spraying process was determined by the weight increase.

The resulting tablets had a weight of 389.5 mg±8.1 mg. This corresponds to a theoretical applied coating of about 173.5 mg. The tablets obtained had a diameter of 9.9 mm and a height of 5.8 mm. The tablets obtained had a smooth surface.

The in-process controls gave the following results:

| Time [min] | Weight [mg] | Standard deviation [mg] |
|---|---|---|
| 0 | 216.0 | 3.9 |
| 30 | 226.9 | 4.3 |
| 60 | 238.2 | 4.1 |
| 90 | 255.5 | 6.3 |
| 120 | 274.0 | 5.2 |
| 150 | 290.9 | 3.7 |
| 180 | 309.5 | 6.8 |
| 210 | 331.8 | 8.0 |
| 240 | 350.1 | 7.2 |
| 270 | 373.6 | 7.9 |
| 300 | 389.5 | 8.1 |

The fracture resistance of 10 of the tablets obtained was examined with an instrument for testing fracture resistance (Schleuniger Type 6D, Dr. Schleuniger Pharmatron AG, Solothurn, Switzerland). The mean fracture resistance was 320 N, the individual values measured were between 280 and 390 N.

The tablets obtained were tested for abrasion in accordance with USP 31 (<1216> Tablet Friability). No abrasion was observed.

The tablets obtained were tested for decomposition time in accordance with USP 31 (<701> Disintegration) using purified water as medium at 37° C. and constantly monitored. After at most 27 minutes, the film coating was completely detached.

The tablets obtained were tested for release in accordance with USP 31 (<711> Dissolution) apparatus 2 (paddle apparatus) at 75 rpm (revolutions by minute) and 900 ml of acetate buffer pH 4.5 with addition of 0.6% of sodium lauryl sulphate as medium at 37° C. 6 tablets were examined. The active ingredient content in the release medium was determined by HPLC using UV detection. After 30 minutes, on average 65% of telmisartan had been released; after 60 minutes, the telmisartan had been released completely from all tablets. The nifedipine release is 10% after 4 hours, 55% after 12 hours and 90% after 24 hours.

Of 10 tablets randomly selected from the tablets obtained, the individual content of telmisartan was in each case determined by HPLC using UV detection. The mean of the individual content was 70.0 mg at a standard deviation of 5.7%, based on the mean. In the test for content uniformity, this resulted in an acceptance value of 13.7%.

The invention claimed is:

1. A pharmaceutical dosage form capsule or tablet comprising:
   a core comprising:
      an osmotic release system comprising nifedipine or nisoldipine and an osmotic membrane comprising cellulose acetate or a mixture of cellulose acetate and polyethylene glycol, wherein the nifedipine or the nisoldipine is released in a controlled manner; and
   a mantle coating around the core, the mantle coating comprising at least one film-forming polymer suitable for the rapid release of active ingredients and an angiotensin II antagonist, wherein the angiotensin II antagonist is released rapidly and wherein the film-forming polymer is partially hydrolyzed polyvinyl alcohol, wherein the thickness of the mantle coating is from 50 to 1500 μm,
   wherein 5 to 17% (by weight) of the nifedipine or nisoldipine is released within 4 hours, 45 to 75% (by weight) of the nifedipine or nisoldipine is released within 12 hours, at least 85% (by weight) of the nifedipine or nisoldipine is released over a period of 24 hours, and the rapid release of active ingredients includes at least 60% (by weight) of the angiotensin II antagonist being released over a period of 30 minutes when assayed according to a USP release method using apparatus 2 (paddle) at 75 revolutions per minute in 900 ml of a suitable medium.

2. The pharmaceutical dosage form according to claim 1, wherein the angiotensin II antagonist is selected from the group consisting of candesartan, losartan, telmisartan, irbesartan, embursartan, eprosartan, valsartan, or olmesartan or a prodrug of one of these angiotensin II antagonists.

3. The pharmaceutical dosage form according to claim 2, where any candesartan is in the form of candesartan cilexetil and any olmesartan is in the form of olmesartan medoxomil.

4. The pharmaceutical dosage form according to claim 1, the nifedipine or nisoldipine is employed in a minimum dose of 5 mg and a maximum dose of 90 mg and the angiotensin II antagonist is employed in a minimum dose of 2 mg and a maximum dose of 500 mg.

5. The pharmaceutical dosage form according to claim 1, wherein the proportion of angiotensin II antagonist in the mantle coating is from 10 to 50%, based on the dry weight of the mantle coating.

6. The pharmaceutical dosage form according to claim 1, wherein the weight of the mantle coating in the dosage form according to the invention is from 20 to 300 mg.

7. The pharmaceutical dosage form according to claim 1, wherein the angiotensin II antagonist is candesartan.

8. The pharmaceutical dosage form according to claim 7, wherein the candesartan is in the form of candesartan cilexetil.

9. The pharmaceutical dosage form acording to claim 8, wherein the amount of nifedipine is 20 mg, and the amount of candesartan cilexetil is 4 mg.

10. The pharmaceutical dosage form according to claim 8, wherein the amount of nifedipine is 20 mg, and the amount of candesartan cilexetil is 8 mg.

11. The pharmaceutical dosage form according to claim 8, wherein the amount of nifedipine is 20 mg, and the amount of candesartan cilexetil is 16 mg.

12. The pharmaceutical dosage form according to claim 8, wherein the amount of nifedipine is 20 mg, and the amount of candesartan cilexetil is 32 mg.

13. The pharmaceutical dosage form according to claim 8, wherein the amount of nifedipine is 30 mg and the amount of candesartan cilexetil is 4 mg.

14. The pharmaceutical dosage form according to claim 8, wherein the amount of nifedipine is 30 mg and the amount of candesartan cilexetil is 8 mg.

15. The pharmaceutical dosage form according to claim 8, wherein the amount of nifedipine is 30 mg and the amount of candesartan cilexetil is 16 mg.

16. The pharmaceutical dosage form according to claim 8, wherein the amount of nifedipine is 30 mg, and the amount of candesartan cilexetil is 32 mg.

17. The pharmaceutical dosage form according to claim 8, wherein the amount of nifedipine is 60 mg, and the amount of candesartan cilexetil is 4 mg.

18. The pharmaceutical dosage form according to claim 8, wherein the amount of nifedipine is 60 mg and the amount of candesartan cilexetil is 8 mg.

19. The pharmaceutical dosage form according to claim 8, wherein the amount of nifedipine is 60 mg, and the amount of candesartan cilexetil is 16 mg.

20. The pharmaceutical dosage form according to claim 8, wherein the amount of nifedipine is 60 mg, and the amount of candesartan cilexetil is 32 mg.

21. The pharmaceutical dosage form according to claim 1, wherein the osmotic release system is an osmotic single-chamber system.

22. The pharmaceutical dosage form according to claim 1, wherein the osmotic release system is a single-chamber system comprising:
the core, comprising:
5 to 50% of the active ingredient nifedipine or nisoldipine,
10 to 50% xanthan,
5 to 40% of a vinylpyrrolidone-vinyl acetate copolymer; and
the osmotic membrane consisting of a water-permeable material which is impermeable for the components of the core and has at least one orifice.

23. The pharmaceutical dosage form according to claim 1, wherein the osmotic release system is an osmotic two-chamber system.

24. The pharmaceutical dosage form according to claim 23, the two-chamber system comprising:
a core having an active ingredient layer, comprising:
5-50% of the nifedipine or the nisoldipine, and
40% to 95% of at least one osmotically active polymer;
an osmosis layer comprising:
40 to 95% of at least one osmotically active polymer, and
5 to 40% of an osmotically active additive; and
an osmotic membrane consisting of a water-permeable material which is impermeable for the components of the core and has at least one orifice.

25. The pharmaceutical dosage according to claim 1, wherein the thickness of the mantle coating is from 75 μm to 1200 μm.

26. The pharmaceutical dosage according to claim 1, wherein the thickness of the mantle coating is from 100 μm to 1000 μm.

* * * * *